US010918710B2

(12) United States Patent
Yu et al.

(10) Patent No.: US 10,918,710 B2
(45) Date of Patent: Feb. 16, 2021

(54) TEMPERATURE-SENSITIVE ATTENUATED FMDV STRAINS, CONSTRUCTION METHOD AND APPLICATION THEREOF

(71) Applicant: HARBIN VETERINARY RESEARCH INSTITUTE, CHINESE ACADEMY OF AGRICULTURAL SCIENCES, Harbin (CN)

(72) Inventors: Li Yu, Harbin (CN); Decheng Yang, Harbin (CN); Haiwei Wang, Harbin (CN); Guohui Zhou, Harbin (CN)

(73) Assignee: HARBIN VETERINARY RESEARCH INSTITUTE. CHINESE ACADEMY OF AGRICULTURAL SCIENCES, Harbin (CN)

( * ) Notice: Subject to any disclaimer, the term of this patent is extended or adjusted under 35 U.S.C. 154(b) by 0 days.

(21) Appl. No.: 16/461,004

(22) PCT Filed: Nov. 20, 2017

(86) PCT No.: PCT/CN2017/111936
§ 371 (c)(1),
(2) Date: May 15, 2019

(87) PCT Pub. No.: WO2018/090994
PCT Pub. Date: May 24, 2018

(65) Prior Publication Data
US 2019/0275139 A1  Sep. 12, 2019

(30) Foreign Application Priority Data
Nov. 21, 2016 (CN) .......................... 2016 1 1047932

(51) Int. Cl.
| | |
|---|---|
| *A61K 39/135* | (2006.01) |
| *A61P 31/14* | (2006.01) |
| *C12N 15/113* | (2010.01) |
| *C12N 7/00* | (2006.01) |
| *C12N 7/04* | (2006.01) |
| *A61K 39/00* | (2006.01) |

(52) U.S. Cl.
CPC ............ *A61K 39/135* (2013.01); *A61P 31/14* (2018.01); *C12N 7/00* (2013.01); *C12N 7/04* (2013.01); *C12N 15/113* (2013.01); *A61K 2039/53* (2013.01); *A61K 2039/552* (2013.01)

(58) Field of Classification Search
None
See application file for complete search history.

(56) References Cited

U.S. PATENT DOCUMENTS

| | | | |
|---|---|---|---|
| 2003/0158141 A1* | 8/2003 | Gromeier | ............... C12N 15/86 514/44 R |
| 2019/0275139 A1* | 9/2019 | Yu | .......................... A61P 31/14 |

FOREIGN PATENT DOCUMENTS

| | | |
|---|---|---|
| CN | 101724636 A | 6/2010 |
| CN | 101838658 A | 9/2010 |
| CN | 103849637 A | 6/2014 |
| CN | 106318955 A | 1/2017 |

OTHER PUBLICATIONS

Sequence alignment of SEQ ID No. 1 with GenEmbl db No. HM008917 by Yang et al 2011.*
Sun et al. (Journal of General Virology, available online Apr. 1, 2016; 97: 901-911).*
Yang et al. (Journal of Virology. Aug. 2020; 94 (16): e00990-20).*
Fernandez-Miragall et al. (Virus Research. 2009; 138: 172-182.*
Marvin J. Grubman, Barry Baxt. Foot-and-Mouth Disease. Clinical Microbiology Reviews. Apr. 2004. 17:465-493. vol. 17 No. 2.
Juan M. Pacheco, P. W. Mason. Evaluation of Infectivity and Transmission of Different Asian Foot-and-Mouth Disease Viruses in Swine. Journal of Veterinary Science. 2010. 11(2), pp. 133-142.
Gao,Rongyuan et al. , Encephalomyocarditis virus IRES replacement reveals no effect on the replication and virulence of FMDV. Chinese Journal of Preventive Veterinary Medicine. Nov. 30, 2015, ISSN:1008-0589, pp. 834-837. vol. 37 No. 11, China Academic Journal Electronic Publishing House.
Sun,Chao , IRES Element Determines Cell Tropism of Foot-and-mouth Disease Virus and Its Molecular Mechanism, China Master's Theses Full-Text Database, Apr. 2014.
Mateo, Roberto, et al., Engineering Viable Foot-and-Mouth Disease Viruses with Increased Thermostability as a Step in the Development of Improved Vaccines, Journal of Virology, 82(24), Dec. 31, 2008, ISSN:0022-538X, pp. 12232-12240.
L.J. Reed et al. A Simple Method of Estimating Fifty Per Cent End Points, The American Jounal of Hygiene, May 1938 vol. 27 No.3 pp. 493-497.
Gao Rongyuan et al. Research on the Determination of IRES Element on FMDV Cell Tropism and the Molecular Mechanism thereof, China Master's Theses Full-Text Database, No. 11, Nov. 15, 2014, ISSN:1674-0246, D050-59.

* cited by examiner

*Primary Examiner* — Shanon A. Foley
(74) *Attorney, Agent, or Firm* — Bayramoglu Law Offices LLC

(57) ABSTRACT

A temperature-sensitive attenuated FMDV strain, construction method and applications thereof. The construction method of the temperature-sensitive attenuated FMDV strain is as follows. Mutating a cytosine on K region loop of IRES domain 4 of an FMDV genome to a guanine or an adenine to obtain the temperature-sensitive attenuated FMDV strain, or replacing a K region of IRES domain 4 of an FMDV genome with a K region of IRES domain 4 of a bovine rhinovirus genome to obtain the temperature-sensitive attenuated FMDV strain.

9 Claims, 7 Drawing Sheets
Specification includes a Sequence Listing.

TEMPERATURE-SENSITIVE ATTENUATED FMDV STRAINS, CONSTRUCTION METHOD AND APPLICATION THEREOF

CROSS REFERENCE TO THE RELATED APPLICATIONS

This application is the national phase entry of International Application No. PCT/CN2017/111936, filed on Nov. 20, 2017, which is based upon and claims priority to Chinese Patent Application No. 201611047932.7, filed on Nov. 21, 2016, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBBJSY003-Sequence Listing-20200908.txt, dated Sep. 8, 2020, and is 10,768 bytes in size.

TECHNICAL FIELD

The present invention relates to construction of the site-directed mutants, chimeras of foot-and-mouth disease virus (FMDV) genome internal ribosome entry site (IBES) for generation of temperature-sensitive attenuated FMDV strains, and further relates to the application of the constructed temperature-sensitive attenuated FMDV strain as an attenuated vaccine strain for prevention and control of foot-and-mouth disease (FMD) or as a safe virus-seed for producing FMD inactivated vaccine. The present invention belongs to the field of prevention and treatment of FMD.

BACKGROUND

FMD is an acute, febrile, and highly contagious disease caused by FMDV, which mainly infected cloven-hoofed animals such as pigs, cattle, and sheep (Grubman And Baxt. 2004. Clinical Micro. Rev. 17:465-493). Once the disease breaks out, it has serious impacts on international trade and the social economy. Therefore, FMD is internationally known as a political and economic disease and has always been highly emphasized and prioritized by governments.

FMDV is a member of the genus *Aphthovirus* in the family Picornaviridae that exists as seven distinct serotypes: A, O, C, Asia1 and South African Territories type 1 (SAT1), SAT2, and SAT3. There is no immune cross-protection between different serotypes of strains. The genome of FMDV is a single-stranded positive-sense RNA with a length of approximately 8.5 kb and consists of a 5' untranslated region (5' UTR), an open reading frame (ORF) and a 3' UTR. The 5' UTR of FMDV lacks a cap structure, and the initiation of protein translation depends on the internal ribosome entry site (IRES) that is an RNA cis-acting element, which initiates the synthesis of viral proteins by recruiting eukaryotic translational initiation factors and ribosomes. The IRES of FMDV is approximately 450 nt in length, including four domains, and is an essential element for initiating the translation of viral proteins.

Immune vaccination is an important means of controlling the prevalence of FMD. However, the commercialized FMD inactivated vaccine used in China and abroad has the following disadvantages: 1) the use of virulent strains as virus-seeds to produce a vaccine has the risk of virus spread due to incomplete inactivation or virus escape during factory production; 2) inactivated FMDV antigen has poor immunogenicity and short immune protection period, immunized animals are prone to FMDV persistent infections when re-infected with FMDV, and persistently infected animals may become an infection source of re-emergence, which will seriously affect the implementation of FMD immunization and eradication program; 3) FMDV antigens are prone to variability, and the update of the virus-seeds for producing the vaccine cannot keep up with the speed of virus mutation, which will have a great impact on the immune effect of the inactivated vaccine. The research history of human and animal vaccines shows that only attenuated vaccines can induce rapid, strong and long-lasting immune responses, and can completely overcome the shortcomings and deficiencies of inactivated vaccines. By using attenuated vaccines, the smallpox and rinderpest in the world have been successfully eliminated and some viral diseases such as poliomyelitis have been controlled. Although FMD is prevalent in many countries and regions of the world and occasionally breaks out in non-epidemic countries, the widely used vaccine so far is still an inactivated vaccine with short immunization period and high cost, and the safe and effective live attenuated FMDV vaccines have not been successfully developed.

In the past 100 years, researchers have been trying to develop a live attenuated vaccine for the prevention and control of FMD. However, because the virulence-attenuated phenotype of the virus is not stable, attenuated strain could not induce the effective protective immune response, the attenuation degree of attenuated strain is different among different animal species and genera, and the risk of reversion to virulence exists, the FMDV attenuated vaccines have not been successfully developed. In recent years, with the development of molecular virology technology and the extensive research on FMDV, especially the use of FMDV infectious cDNA clones, the determinants of viral virulence can be determined through further studies. Then the specific changes are introduced into the genome of FMDV and the attenuated phenotype thereof is evaluated in vitro and in vivo, thus enabling the development of a live attenuated FMDV vaccine that has good immunogenicity and is successfully attenuated in all natural host. Developing a practical FMDV live attenuated vaccine requires to meet the following conditions: 1) attenuated for all susceptible animals and do not cause clinical symptoms; 2) induces a strong immune response after immunization and provides anti-infective protection to immunized animals; 3) the vaccinated animals do not shed viruses, and the attenuated vaccine strain does not spread between the vaccinated animals and the healthy animal individuals, and cannot reverse to virulence. These required indicators are extremely challenging, but they are a prerequisite for successful research and application of a live attenuated FMD vaccine.

SUMMARY

The present invention provides a method for constructing temperature-sensitive attenuated FMDV strains, including: construction of a full-length cDNA infectious clone of FMDV, obtain the viral RNA by in vivo transcription, transfection of the viral RNA into cells and rescue of the viruses; wherein the cytosine (C) at the 351 position on the K loop region ($^{351}$CUUUAA$^{356}$) of the IRES domain 4 of the FMDV genomic RNA obtained by in vitro transcription is mutated to guanine (G) or adenine (A), the nucleotide sequence of the K loop region after mutation is $^{351}$GUUUAA$^{356}$ or $^{351}$AUUUAA$^{356}$.

Specifically, the present invention provides a temperature-sensitive attenuated FMDV strain obtained by the above-mentioned construction method, which is named rC351G. The rC351G has a high genetic stability and a temperature-sensitive phenotype, which is attenuated for all susceptible cloven-hoofed animals (at body temperature of 38.5-40° C.), and meets the safety requirements of live attenuated vaccines. Pigs were inoculated with the temperature-sensitive attenuated FMDV strain rC351G, and the vaccinated animals do not exhibit any clinical symptoms, but can induce high levels of type-O FMDV neutralizing antibodies and can completely protect the animals from the challenge of heterologous strains of different genotypes of type-O FMDV which are currently prevalent in China. The temperature-sensitive attenuated FMDV strain rC351G has good safety, and the horizontal transmission does not occur between vaccinated pigs and healthy pigs, and the attenuated strain rC351G does not reverse to virulence after continuous passages in the pigs. Therefore, the rC351G can be prepared into a live attenuated vaccine for the prevention and treatment of FMD according to the conventional preparation method of live attenuated vaccine, or be used as a safe virus-seed of the inactivated vaccine for the prevention of FMD.

The present invention submits an *E. coli* host containing a full-length cDNA infectious cloning plasmid of FMDV to a patent-approved institution for preservation, the full-length cDNA infectious cloning plasmids used for rescuing the temperature-sensitive attenuated FMDV strain rC351G. The microbial deposit number is: CGMCC NO.13148; the scientific name is: *Escherichia Coli* (*E. coli*); the deposit time is: Oct. 26, 2016; the depositary institution is: China General Microbiological Culture Collection Center; the deposit address: Institute of Microbiology, Chinese Academy of Sciences, No. 1-3 West Beichen Road, Chaoyang District, Beijing, China.

The present invention provides an IRES mutant for construction of a FMDV temperature-sensitive attenuated strain, the full-length nucleotide sequence thereof is shown in SEQ ID No: 1. The IRES mutant can be used to construct the temperature-sensitive attenuated FMDV strain by using FMDV reverse genetic system. Further, the constructed temperature-sensitive attenuated FMDV strain can be prepared into a live attenuated vaccine for the prevention and treatment of FMD according to the conventional preparation method of live attenuated vaccine. The full-length cDNA infectious clone of the constructed temperature-sensitive attenuated FMDV strain can be rescued to function as a safe virus-seed of inactivated vaccine, or used to construct a FMD RNA vaccine.

The present invention provides a method for constructing another temperature-sensitive attenuated FMDV strain, including: construction of a full-length cDNA infectious clone of FMDV, obtaining the viral RNA by in vivo transcription, transfection of the viral RNA into cells and rescuing of the virus; wherein the IRES domain 4 of the FMDV genomic RNA obtained by in vitro transcription is replaced with the IRES domain 4 of bovine rhinitis B virus (BRBV) genomic RNA.

The present invention provides another temperature-sensitive attenuated FMDV strain obtained by the above mentioned construction method, which is named FMDV(R4). The FMDV(R4) has a high genetic stability and a temperature-sensitive phenotype, the temperature-sensitive property thereof indicates that the FMDV(R4) is attenuated for all susceptible cloven-hoofed animals (at body temperature of 38.5-40° C.), which meets the safety requirements of attenuated strain. Pigs were inoculated with the temperature-sensitive attenuated FMDV strain FMDV(R4), and the vaccinated animals do not exhibit any clinical symptoms, and the horizontal transmission does not occur between vaccinated pigs and healthy pigs. More importantly, the vaccinated pigs do not produce antibodies against FMDV, which indicates that the FMDV(R4) constructed by the present invention, as a virus-seed for FMD inactivated vaccine, has better safety, and the full-length cDNA infectious clone of the FMDV(R4) can also be rescued as a virus-seed of the FMD inactivated vaccine.

The present invention submits an *E. Coli* host containing a full-length cDNA infectious cloning plasmid of FMDV to a patent approved institution for preservation, the full-length cDNA infectious cloning plasmids used for rescuing the temperature-sensitive attenuated FMDV strain FMDV(R4). The microbial deposit number is: CGMCC NO.13149; the scientific name is: *Escherichia Coli* (*E. coli*); the deposit time is: Oct. 26, 2016; the depositary institution is: China General Microbiological Culture Collection Center; the deposit address: Institute of Microbiology, Chinese Academy of Sciences, No. 1-3 West Beichen Road, Chaoyang District, Beijing, China.

The present invention also provides a chimeric IRES obtained by replacing the IRES domain 4 of FMDV with that of bovine rhinovirus, the full-length sequence thereof is shown in SEQ ID No: 2. The chimeric IRES can be used to construct the temperature-sensitive attenuated FMDV strain by using FMDV reverse genetic system. Further, the constructed temperature-sensitive attenuated FMDV strain can be prepared into FMD inactivated vaccine for the prevention and treatment of FMD according to the conventional preparation method of FMD inactivated vaccine. The full-length cDNA infectious clone of the constructed temperature-sensitive attenuated FMDV strain can be rescued as a safe virus-seed of the FMD inactivated vaccine.

The present invention further provides a method for constructing a temperature-sensitive attenuated FMDV strain, including: construction of a full-length cDNA infectious clone of FMDV, obtaining the viral RNA by in vivo transcription, transfection of the viral RNA into cells and rescuing of the virus where in the K region of IRES domain 4 of FMDV obtained by in vitro transcription is replaced with the K region of IRES domain 4 of bovine rhinitis B virus (BRBV).

A temperature-sensitive attenuated FMDV strain obtained by the above-mentioned construction method is named rdK. The temperature-sensitive attenuated FMDV strain rdK provided by the present invention has a temperature-sensitive phenotype and a high genetic stability, the temperature-sensitive property thereof indicates that the rdK is attenuated for all susceptible cloven-hoofed animals (at body temperature of 38.5-40° C.), which meets the safety requirements of attenuated strain. The present invention inoculates the temperature-sensitive attenuated FMDV strain rdK into pigs, and the vaccinated animals do not exhibit any clinical symptoms, and the horizontal transmission does not occur between the vaccinated pig and the healthy pig. More importantly, the vaccinated pigs do not produce antibodies against FMDV, which indicates that the rdK constructed by the present invention, as a virus-seed for FMD inactivated vaccine, has better safety. Therefore, the full-length cDNA infectious clone of the rdK strain can be rescued as a safe virus-seed of the FMD inactivated vaccine.

The present invention submits an *E. coli* host containing a full-length cDNA infectious cloning plasmid of FMDV to a patent-approved institution for preservation, the full-length cDNA infectious cloning plasmids used for rescuing the temperature-sensitive attenuated FMDV strain rdK. The microbial deposit number is: CGMCC NO.13150; the scientific name is: *Escherichia Coli* (*E. coli*); the deposit time is: Oct. 26, 2016; the depositary institution is: China General Microbiological Culture Collection Center; the deposit address: Institute of Microbiology, Chinese Academy of Sciences, No. 1-3 West Beichen Road, Chaoyang District, Beijing, China.

The present invention provides a chimeric IRES obtained by replacing the K region of IRES domain 4 of FMDV genomic RNA with that of bovine rhinitis B virus (BRBV) genomic RNA, the full-length sequence thereof is shown in SEQ ID No: 3. The chimeric IRES can be used to construct the temperature-sensitive attenuated FMDV strain by using conventional FMDV reverse genetic technical means in the field.

Detailed Description of the Technical Solution of the Present Invention

The present invention uses the type-O FMDV reverse genetic system to replace the IRES domain 4 of FMDV with the corresponding IRES domain of BRBV, successfully constructing and rescuing the IRES chimeric mutant FMDV (R4). The virulence of IRES chimeric virus FMDV(R4) was determined by using 3-day-old suckling mice as models, and the virulence thereof decreased by about 100 times compared with that of the parental virus FMDV(WT), demonstrating that IRES domain 4 is the determinant element of the virulence of FMDV.

In order to determine whether the replication of FMDV (R4) is temperature-sensitive, the one-step growth curves of FMDV(R4) at different temperatures on two kinds of cells, hamster-derived BHK-21 and porcine-derived IBRS-2, were plotted. The experiment results confirmed that the IRES chimeric attenuated strain FMDV(R4) is a temperature-sensitive mutant, and this temperature-sensitive property is particularly obvious in the porcine-derived IBRS-2 cells of susceptible host animals.

In order to further analyze the molecular determinants of the temperature-sensitive attenuated phenotype of the IRES chimeric virus FMDV(R4), the present invention uses the type-O FMDV reverse genetic operating system to replace the J, K, or N subdomains in IRES domain 4 of FMDV with the corresponding subdomains of BRBV IRES. The IRES J, K or N subdomain chimeric FMDV mutant strains were successfully constructed and rescued, and named rdJ, rdK or rdN. The replication dynamics of the three chimeric viruses at different temperatures were determined and analyzed, and the one-step growth curves were plotted. The results showed that whether in BHK-21 cells or in IBRS-2 cells, or at different temperatures of 33° C., 37° C. and 41° C., the chimeric viruses rdJ, rdN and the parental virus FMDV(WT) had similar proliferation properties. However, the chimeric virus rdK had the similar replication ability to the parental virus FMDV(WT) only at 33° C. and 37° C. in BHK-21 cells, but the replication ability thereof significantly decreased at 41° C., which decreased by about 100 times compared with that of the parental virus FMDV(WT). In IBRS-2 cells, the replication ability of chimeric virus rdK significantly decreased even at 37° C., which decreased by 1,000 times compared with that of the parental virus, and the replication ability of rdK was almost lost at 41° C. The replication property of the chimeric virus rdK (rather than rdJ and rdN) is consistent with the replication property of the chimeric virus FMDV(R4), indicating that the K region of IRES domain 4 determines the temperature-sensitive property of the chimeric virus FMDV(R4). At the same time, the virulence test results in the suckling mice showed that the virulence of rdK decreased by about $10^6$ times compared with the virulence of FMDV(WT). To sum up, these results indicated that the K region of IRES domain 4 determines the temperature-sensitive attenuated phenotype of the IRES chimeric virus FMDV(R4).

The K regions of the IRES domain 4 of FMDV and BRBV are respectively composed of a stem-loop structure. In order to determine the region in the stem-loop structure of the K region associated with the temperature-sensitive attenuated phenotype of FMDV, the present invention uses the reverse genetic operating technique to replace the stem and loop of the K region of the FMDV IRES with the stem and loop of the K region of the BRBV IRES, respectively. The two chimeric viruses rescued were named rK(Stem) and rK(Loop), respectively, and their replication dynamics at different temperatures and in different cells were determined. Whether in BHK-21 cells or IBRS-2 cells, or at different temperatures of 33° C., 37° C. and 41° C., the chimeric virus rK(Stem) has similar proliferation properties to the parental virus FMDV(WT). However, the replication abilities of chimeric virus rK(Loop) in the two kinds of cells gradually decreased with the increase of temperature, and replication properties thereof were extremely similar to those of rdK. The above results indicated that the loop structure of the K region of IRES domain 4 determined the temperature sensitivity of the chimeric virus FMDV(R4). When virulence of rK(Loop) was tested, it was found that the virus was unstable in suckling mice. A T351C reverse mutation occurred at the 351 position of IRES, which is consistent with the reverse mutation occurred at the 351 position of IRES after the virus was over multiple in vitro passages in BHK-21 cells. This reverse mutation results in the loop structure of the K region of the rK(Loop) being close to the loop structure of the K region of the parental virulent strain, and therefore the virulence of the mutant rK(Loop) to the suckling mouse restored to the level of the parental virus.

The loop ($-^{351}$CUUUAA$^{356}$-) of the IRES K region of FMDV has a similar structure to the loop (-UUUAC-) of the IRES K region of BRBV, and their main differences are as follows: at the 351 position of the initiation site of the loop structure of the K region of the FMDV IRES where there is an extra nucleotide C; and at the 356 position of the loop structure of the K region of the FMDV IRES where there is a nucleotide A, while at the 356 position of the loop structure of the K region of the BRBV IRES where there is a nucleotide C. In order to precisely determine the molecular factors that determine the temperature-sensitive phenotype of FMDV, the present invention first mutated the nucleotide A at 356 position of FMDV IRES to the nucleotide C at 356 position of BRBV IRES, and the constructed and rescued mutant virus was named rA356C. The replication dynamics of the mutant at different temperatures showed that the replication abilities of rA356C in the two kinds of cells, BHK-21 and IBRS-2, were similar to those of the parental virus FMDV(WT) at temperatures of 33° C., 37° C. and 41° C., which indicated that the nucleotide A356 of FMDV IRES is irrelevant to the temperature-sensitive phenotype of FMDV.

In order to determine the correlation between the nucleotide C351 of IRES and the temperature-sensitive phenotype of FMDV, the present invention makes the following four mutations for the nucleotide C at the 351 position:

(1) a deletion of nucleotide C351; (2) nucleotide C351 mutated to nucleotide A; (3) nucleotide C351 mutated to nucleotide G; (4) nucleotide C351 mutated to nucleotide U.

The final test results showed that the mutation schemes (1) and (4) failed to rescue the virus due to the destruction of the loop structure of the IRES, while the mutation schemes (2) and (3) can rescue the virus due to the of invariance of the IRES loop structure, and the rescued IRES-mutated viruses are named rC351A and rC351G, respectively. The replication dynamics of the two virus mutants with IRES point mutation C351A or C351G were measured at different temperatures. The results showed that the replication properties of the two IRES C351 site mutated viruses are similar to those of the IRES chimeric virus rK(Loop), which indicated that this site is the molecular determinant of the temperature-sensitive phenotype of the IRES chimeric FMDV. The present invention also found that the virulence of the IRES C351-site mutated viruses significantly decreased in the suckling mice. Compared with the wild-type virus, the virulence of rC351G decreased by about 10,000 times and the virulence of rC351A decreased by 1,000 times. The above results finally indicated that the nucleotide C at 351-site on the loop of the K region of IRES domain 4 determined the temperature-sensitive attenuated phenotype of FMDV.

In order to determine the genetic stability of FMDV temperature-sensitive attenuated strains, in the present invention, the IRES chimeric or site-directed mutagenesis recombinant viruses FMDV(R4), rdK, rK(Loop), rC351G, rC351A and the parental virus FMDV(WT) were continuously passaged for 20 times in BHK-21 cells, and the IRES sequences of 20th passage viruses were determined. The results showed that the IRES chimeric or site-directed mutagenesis temperature-sensitive attenuated FMDV strains FMDV(R4), rdK, rC351G and rC351A had high genetic stability; whereas, the IRES K-region loop chimeric temperature-sensitive attenuated FMDV strain rK(Loop) was unstable, when it was passed to the $20^{th}$ passage, the reverse mutation was occurred in some of the virus, and when it was passed to the $25^{th}$ passage, the reverse mutation was occurred in the whole virus group.

In order to verify that the C351G mutation of IRES also determines the temperature-sensitive attenuated phenotype of other serotypes of FMDV strains, the present invention further uses the full-length cDNA infectious clone of the type-A and type-Asia1 FMDV to construct and rescue mutant strains with the nucleotide substitution C351G occurred in the IRES, which are named A-rC351G and Asia1-rC351G, respectively. The temperature sensitivities of the above IRES mutated strains were determined, and the results showed that the replication abilities of both A-rC351G and Asia1-rC351G in BHK-21 and IBRS-2 cells decreased with the increase of temperature, which indicated that the C351G mutation in the IRES also enabled other serotypes of FMDV strains to obtain the temperature-sensitive phenotype. In addition, the virulence test results of A-rC351G and Asia1-rC351G in suckling mice showed that the C351G mutation in the IRES could also reduce the virulence of the type-A and type-Asia1 FMDV to suckling mice by at least 10,000 times, indicating that the temperature-sensitive attenuated phenotypes of the three serotypes of FMDV strains prevalent in China, type-O, type-A and type-Asia1, were determined by IRES C351. Since the C351 site of IRES is conserved in all FMDV strains, it was determined that the IRES C351 is a molecular determinant of the temperature-sensitive attenuated phenotype of all serotypes of FMDV strains.

The present invention, through structural and functional studies and sequence alignment analysis, finally confirms that the nucleotide C351 on the loop of the K region of FMDV IRES domain 4 determines the temperature-sensitive attenuated phenotype of all seven serotype FMDV strains. The FMDV attenuated mutants mutated with C351G substitution occurred in IRES shows high genetic stability when continuous passaged in cells, and all of these virus mutants have the temperature-sensitive phenotype, and thus attenuated for all susceptible cloven-hoofed animals (at body temperature of 38.5-40° C.), which meets the safety requirements of live attenuated vaccines.

The temperature-sensitive attenuated mutant strains of FMDV provided by the invention show safety and effectiveness after being inoculated into susceptible animals and challenging, and have a significant security advantage, which can be used as virus-seed of the live attenuated vaccine or inactivated vaccine to prevent FMD. The IRES mutant or the chimeric IRES sequence and full-length cDNA infectious clone of the temperature-sensitive attenuated FMDV strain provided by the present invention can be used to prepare the live FMD attenuated vaccine, used as virus-seed to prepare the FMD inactivated vaccine, or used to prepare the FMD RNA vaccine.

BRIEF DESCRIPTION OF THE DRAWINGS

FIG. 1 is a graph showing test results of the virulence of IRES domain 4 chimeric virus FMDV(R4) in suckling mice.

FIG. 2 is a graph showing one-step growth curves of IRES chimeric virus FMDV(R4) and its parental virus at different temperatures.

FIG. 3 is a graph showing one-step growth curve of IRES domain 4 subdomain chimeric FMDV mutant.

FIG. 4 is a graph showing one-step growth curves of IRES chimeric FMDV mutants rK(Stem) and rK(Loop).

FIG. 5 is a graph showing one-step growth curves of IRES site-directed mutagenesis FMDV mutants rC351G and rC351A.

FIG. 6 is a graph showing the genetic stability (A) and temperature sensitivity (B) of the IRES chimeric and site-directed FMDV mutants in BHK-21 cells.

FIG. 9 is a graph showing the analysis of the IRES C351G mutant-mediated translation initiation efficiency: the IRES-mediated translation efficiency (A) is detected by using a replicon system; the expression amount of VP2 protein and virus titers are detected in the BHK-21 cells (B) and IBRS-2 cells (C) infected with the virus.

FIG. 10 is a graph showing test results of the virulence of the several temperature-sensitive attenuated strains and wild-type parental viruses FMDV(WT) in the inoculated pigs.

DETAILED DESCRIPTION OF THE EMBODIMENTS

Figure 7:
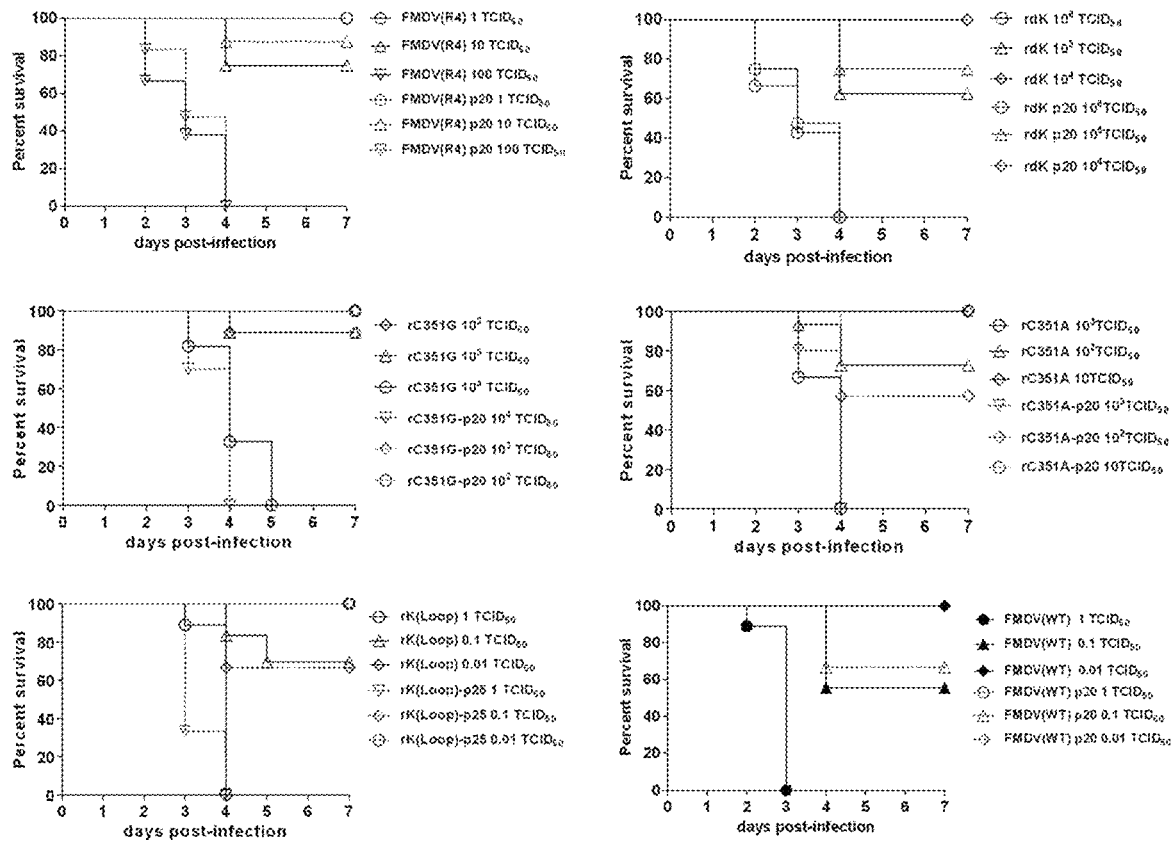
FIG. 7 is a graph showing the virulence of temperature-sensitive FMDV mutant in suckling mice.

The present invention will be further described below with reference to the specific embodiments, and the advantages and features of the present invention will become clearer with the description. However, it should be understood that the embodiments are merely illustrative rather than intended to limit the scope of the present invention. It should be understood by those of ordinary skill in the art that the details and forms of the present invention may be modified or substituted without departing from the spirit and scope of the present invention, however, such modifications or substitutions fall within the scope of the present invention.

1. Materials and Methods 1.1 Cells, Vectors and Viruses

BHK-21 cells and IBRS-2 cells were cultured at 37° C. under the condition of containing 5% $CO_2$, and the culture medium was DMEM containing 10% foetal bovine serum (FBS). pOK-12 vector was a generous gift from the Messing (1991); type-O FMDV O/YS/CHA/05 strain (GenBank accession number: HM008917) and the infectious cDNA clone pYS of the virus can be obtained by the method disclosed in the literature (Chinese Patent Publication No.: CN101838658A (ZL201010160669.9)); an infectious cDNA clone of the type-Asia 1 FMDV Asia1/YS/CHA/05 strain (GenBank accession number: GU931682) can be obtained by the method disclosed in the literature (Chinese Patent Publication No. CN101724636A (ZL200810171258.2)); type-A FMDV A/VN/03/2009 strain (GenBank accession number: GQ406249) was kept by the inventor's laboratory.

1.2 Primers

According to the bovine rhinovirus IRES gene sequence (GenBank accession number: EU236594) and the genomic sequence of the FMDV O/YS/CHA/05 strain, the primers (Tab. 1) used to amplify different domains in IRES of two viruses and site-directed mutagenesis primers (Tab. 2) were designed and were synthesized in Shanghai Yingjun Biotechnology Co., Ltd.

TABLE 1

Primers for constructing IRES chimeric virus and sequences thereof

| Primer Sequence (5'→3') | | Sequence (5'→3') |
|---|---|---|
| 4N-1:U | SEQ ID NO: 4 | CGCAGATCTTAATACGACTCACTATAGG TTGAAAGGGGCGTTAGGGTCTC |
| 4N-1:L | SEQ ID NO: 5 | CTCGGGGTACCTGAAGGGCATCCTTAGG CTGTCACCAGTGGTTGAGTACCAGTATC |
| 4N-2:U | SEQ ID NO: 6 | TGGTGACAGCCTAAGGATGCCCTTCAGG TACCCCGAGGTAACACGCGAC |
| 4N-2:L | SEQ ID NO: 7 | GGCCTCCGGTCACCTATTCAGCTTAGAC GTTTTTAAACCAGGCGCTTTT |
| 4N-3:U | SEQ ID NO: 8 | CGGAGGCCGGCACCTTTCCTTCGAACAA CTGTCTTTAACC |
| 4N-3:L | SEQ ID NO: 9 | GAGGATATCGCTAGCTTTGAAAACCAGT CGTTG |
| 4J-1:U | SEQ ID NO: 10 | CGCAGATCTTAATACGACTCACTATAGG TTGAAAGGGGCGTTAGGGTCTC |
| 4J-1:L | SEQ ID NO: 11 | TTGTTACCCCGGGGTACCTGGAGGGCAT CCTTAGCCTGTCACCAGT |
| 4J-2:U | SEQ ID NO: 12 | CGCAGATCTTAATACGACTCACTATAGG TTGAAAGGGGCGTTAGGGTCTC |
| 4J-2:L | SEQ ID NO: 13 | TCCTCAGATCCCGGGTGTCACTTGTTAC CCCGGGGTACCT |
| 4J-3:U | SEQ ID NO: 14 | CACCCGGGATCTGAGGAGGGGACTGGGG CTTCTTTAAAAGCG |
| 4J-3:L | SEQ ID NO: 15 | GAGGATATCGCTAGCTTTGAAAACCAGT CGTTG |
| 4K-1:U | SEQ ID NO: 16 | CGCAGATCTTAATACGACTCACTATAGG TTGAAAGGGGCGTTAGGGTCTC |
| 4K-1:L | SEQ ID NO: 17 | GCTTTTTAAACTACGTAAAGTAGTCCCC TTCTCAGATCCCGAGTGT |
| 4K-2:U | SEQ ID NO: 18 | CTTTACGTAGTTTAAAAAGCTTCTACGC CTGAATAGGTGACC |
| 4K-2:L | SEQ ID NO: 19 | GAGGATATCGCTAGCTTTGAAAACCAGT CGTTG |

TABLE 2

Primers and sequences for site-directed mutagenesis

| Primer | Sequence (5'→3') | Sequence (5'→3') |
|---|---|---|
| Loop-U | SEQ ID NO: 20 | CTCGGGATCTGAGAAGGGGA CTGGGGCTTTTTACAAGCGC CTGGTTTAAAAAGCTTC |
| Loop-L | SEQ ID NO: 21 | GAAGCTTTTTAAACCAGGCG CTTGTAAAAGCCCCAGTCC CCTTCTCAGATCCCGAG |
| Stem-U | SEQ ID NO: 22 | CACTCGGGATCTGAGAAGGG GACTACCTTTAAGTAGTTTA AAAAGCTTCTACGCCTG |
| Stem-L | SEQ ID NO: 23 | CAGGCGTAGAAGCTTTTTAA ACTACTTAAAGGTAGTCCCC TTCTCAGATCCCGAGTG |
| C351G-U | SEQ ID NO: 24 | CTCGGGATCTGAGAAGGGGA CTGGGGCTTGTTTAAAAGCG CCTGGTTTAAAAAGCTTC |
| C351G-L | SEQ ID NO: 25 | GAAGCTTTTTAAACCAGGCG CTTTTAAACAAGCCCCAGTC CCCTTCTCAGATCCCGAG |
| C351A-U | SEQ ID NO: 26 | CTCGGGATCTGAGAAGGGGA CTGGGGCTTATTTAAAAGCG CCTGGTTTAAAAAGCTTC |
| C351A-L | SEQ ID NO: 27 | GAAGCTTTTTAAACCAGGCG CTTTTAAATAAGCCCCAGTC CCCTTCTCAGATCCCGAG |
| C351T-U | SEQ ID NO: 28 | CTCGGGATCTGAGAAGGGGA CTGGGGCTTTTTTAAAAGCG CCTGGTTTAAAAAGCTTC |
| C351T-L | SEQ ID NO: 29 | GAAGCTTTTTAAACCAGGCG CTTTTAAAAAAGCCCCAGTC CCCTTCTCAGATCCCGAG |
| InsertC351-U | SEQ ID NO: 30 | CGGGATCTGAGAAGGGGACT ACCTTTACGTAGTTTAAAAA GCTTCTACGCCTGAATAG |
| InsertC351-L | SEQ ID NO: 31 | CAGGCGTAGAAGCTTTTTAA ACTACGTAAAGGTAGTCCCC TTCTCAGATCCCGAGTGT |

TABLE 2-continued

Primers and sequences
for site-directed mutagenesis

| Primer | Sequence (5'→3')Sequence (5'→3') | |
| --- | --- | --- |
| deltaC351-U | SEQ ID NO: 32 | CTCGGGATCTGAGAAGGGGA CTGGGGCTTTTTAAAAGCGC CTGGTTTAAAAAGCTTC |
| deltaC351-L | SEQ ID NO: 33 | GAAGCTTTTTAAACCAGGCG CTTTTAAAAAGCCCCAGTCC CCTTCTCAGATCCCGAG |
| TypeA-G351-U | SEQ ID NO: 34 | CTCGGGATCTGAGAAGGGGA CTGGGGCTTGTATAAAGCG CCCAGTTTAAAAAGCTTC |
| TypeA-G351-L | SEQ ID NO: 35 | GAAGCTTTTTAAACTGGGCG CTTTTATACAAGCCCCAGTC CCCTTCTCAGATCCCGAG |
| Asia1-G351-U | SEQ ID NO: 36 | CTCGGGATCTGAGAAGGGGA CCGGGACTTGTTTAAAAGTG CCCGGTTTAAAAAGCTTC |
| Asia1-G351-L | SEQ ID NO: 37 | GAAGCTTTTTAAACCGGGCA CTTTTAAACAAGTCCCGGTC CCCTTCTCAGATCCCGAG |

1.3 Construction of IRES-Chimeric FMDV Infectious Clone Plasmids

An IRES-chimeric FMDV full-length infectious cDNA clone, in which the subdomain N of FMDV IRES domain 4 was replaced with that of the BRBV, was constructed using fusion PCR method. The specific method is as follows: first, using plasmid pYS as a template, 4N-1:U and 4N-1:L as primers to amplify fragment A; using synthetic BRBV IRES gene as a template, 4N-2:U and 4N-2: L as primers to amplify fragment B; and using pYS plasmid as a template, 4N-3:U, 4N-3:L as primers to amplify fragment C. Using the purified PCR amplified fragments A, B, and C as templates, and 4N-1:U and 4N-3:L as primers to perform fusion PCR to amplify the FMDV 5' gene fragment containing partial BRBV IRES substitution, the fragment size is approximately 1.9 Kb. The fragment was recovered from the agarose gel, double digested with Bgl II and Nhe I, and cloned into pYS vector, the correct clone identified by sequencing was named p(dN). Similarly, the full-length FMDV infectious cDNA cloning plasmids containing the BRBV IRES domain4 subdomains J and K were constructed respectively using the primers in Tab. 1, and named p(dJ) and p(dK).

1.4 Construction of A-Type FMDV Full-Length cDNA Infectious Clone

According to the results of whole genome sequencing of foot-and-mouth disease virus A/QSA/CHA/09 strain, the full length of the genome was synthesized by the method of artificially synthesizing genes, and the T7 promoter sequence and Spe I restriction site (5'act agt TAA TAC GAC TCA CTA TAGGG 3'; SEQ ID NO: 40) were introduced at the 5' end of the whole genome cDNA, an EcoR V restriction site (gat atc) was introduced at the 3' end of the whole genome cDNA, which is used for linearization of whole genome cDNA. After restriction digested with restriction endonucleases Spe I and EcoR V, the whole genome was cloned into the low copy vector pOK12, the constructed infectious cDNA clone was named pQSA.

1.5 Site-Directed Mutagenesis

According to the instructions of Quik Change® Site-Directed Mutagenesis Kit, through the PCR technique, the mutation sites were introduced into the infectious cDNA clones using the primers in Tab.2, respectively. PCR amplification procedure: 94° C. for 4 min; 94° C. for 30 s, 68° C. for 9 min, for 18 cycles; 72° C. for 10 min. After the amplification is completed, purifying the PCR products. Degrading the methylated template of the PCR products by Dpn I (at 37° C. for 1 h), transferring the treated PCR products into DH5a competent cells, selecting the bacterial clones, and the correct recombinant plasmids identified by sequencing were named pK(loop), pK(stem), pC351G, pC351A, pC351T, pΔC351, pIn-351C, pA-rC351G, pAsia1-rC351G.

1.6 Rescue of the Virus

After restriction digested and linearized by restriction endonuclease EcoR V, the recombinant plasmids p(dN), p(dJ) and p(dK), pK(loop), pK(stem), pC351G, pC351A, pC351T, pΔC351, pIn-351C, pA-rC351G, pAsia1-rC351G were subjected to the in vitro transcription according to the instruction of RiboMAX™ Large Scale RNA Production Systems-T7 kit. The reaction mixture is: 6 μL 25 mmol/L rNTP, 4 μL 5× buffer, 2 μL T7 RNA polymerase, 8 μL (2 μg) EcoRV linearized recombinant plasmid, a total volume of 20 μL. After thoroughly mixed, the reactants were incubated at 37° C. for 2.5 h, digested with RNase-Free DNase for 15 min, removing the DNA template, and the transcript products were purified by phenol chloroform extracting method. When BHK-21 cells in 6-well plates grew to 60%-90% monolayer, washing the cells twice with PBS and adding 1.5 mL of DMEM containing 2% FBS. Transfecting the RNA obtained by in vitro transcription into BHK-21 cells to rescue the virus according to the transfection kit instructions of Effectene® Transfection Reagent (Qiagen). Culturing the transfected cells at 37° C. under the condition of 5% $CO_2$, observing cytopathicity effect (CPE), the virus was harvested in about 3 days, after repeatedly freezing and thawing for 3 times, the virus was inoculated into fresh BHK-21 cells until the virus produced a stable CPE. The correct mutant strains of the recombinant virus identified by full-length genome sequencing were used for subsequent experiments. The rescued viruses were named rdN, rdJ, rdK, rK(loop), rK(stem), rC351G, rC351A, rIn-351C, A-rC351G, and Asia1-rC351G, respectively.

1.7 One-Step Growth Curve

Wild-type FMDV, recombinant IRES chimeric virus and IRES site-directed mutant virus were inoculated into BHK-21 and IBRS-2 cells at a MOI of 0.05, and adsorbed for 1 h at 33° C., 37° C., 41° C., respectively, then washed with PBS to remove the unadsorbed virus, and DMEM containing 2% FBS was added to maintain the culture, the virus was harvested 4 h, 8 h, 12 h, 16 h, 20 h, 24 h, 28 h, 32 h, 40 h after inoculation, the $TCID_{50}$ titers of the virus harvested at different time points were measured, and the average value of virus $TCID_{50}$ titers was calculated after repeating the measurement three times at each time point. The one-step growth curve of virus replication at different temperatures was plotted with the time of virus infecting cells as the abscissa and the logarithmic value of $TCID_{50}$ titers at different time points as the ordinate.

1.8 Virus Passage and Genetic Stability Test

The wild-type FMDV, IRES-chimeric virus rK (loop), the point mutation viruses rC351A and rC351G were inoculated into BHK-21 cells to react for 1 h, washing with PBS twice, and adding DMEM containing 2% FBS to maintain the culture. Harvesting the viruses until the appearance of CPE. Passing down to continuous passage for 20 passages after repeatedly freezing and thawing for 3 times. Extracting the RNA of viruses every 5 passages for RT-PCR amplification and sequencing.

1.9 FMDV Luciferase Replicons and Luciferase Assay

The 96-well plates of the BHK-21 cells and IBRS-2 cells transfected with the replicon RNA of IRES-chimeric viruses were maintained at 33° C., 37° C. or 41° C. Collecting and lysing the cells after 12 h, and measuring the Rluc activity on a GloMax luminometer according to the instructions of *Renilla* luciferase assay kit of *Renilla*-Glo™ Luciferase Assay System, the reaction system is that per 10 µL of cell lysate buffer was added with 50 µL of reaction solution, parameters are: 2s of read-ahead delay, and 10s of detection time.

1.10 Western Blot

BHK-21 cells or IBRS-2 cells inoculated with 100 $TCID_{50}$ wild-type FMDV and its recombinant virus were cultured for 12 h and then harvested, after lyse treatment, the protein samples were separated by SDS-PAGE, and then transferred to a nitrocellulose membrane. After blocking with 5% skim milk, the membrane was incubated with the primary antibodies MAb 4B2 (diluted at a ratio of 1:1000) at 37° C. for 1 h. After washing with PBST, HRP-labeled rabbit anti-mouse IgG (diluted at a ratio of 1:5000) was added as the secondary antibody, and reacted at 37° C. for 1 h, the DAB solution was added for color development after washing. In addition, the internal reference selected β-Actin antibody (diluted at a ratio of 1:1000) as the primary antibody, and HRP-labeled goat anti-mouse IgG (diluted at a ratio of 1:10000) was used as the secondary antibody.

1.11 Virulence Test in Suckling Mice

The virus was serially gradient diluted in 10-fold with sterilized PBS, and 3-day-old BALB/c suckling mice were selected and randomly divided into groups with 5 mice in each group. Each strain was inoculated successively with virus diluted in 3-gradient, each suckling mouse was injected cervicodorsally with 200 µL of virus solution, and the negative control group were injected with the equal amount of PBS. After continuous observation for 7 days, the survival curve of the suckling mice was plotted with the death time of the suckling mice as the abscissa and with the survival rate of the suckling mice as the ordinate.

1.12 Virulence Test, Safety Test, Vaccination and Challenge Test in Pig

Virulence Test

Twenty of 20-30 kg FMDV serum antibody-negative healthy pigs were randomly divided into 4 groups with 5 in each group. Three pigs in one group were injected intramuscularly at cervical part with wild-type viral strain FMDV (WT) at a dose of $10^5$ $TCID_{50}$/pig, in the other three groups, three pigs in each group were injected intramuscularly at cervical part with IRES mutant strains rC351G, FMDV (R4) or rdK at a dose of $10^6$ $TCID_{50}$/pig, 1 day post-inoculation (dpi), two pigs were placed in each group as cohabiting animals. Within 7 days after inoculation, measuring the body temperature of each pig, observing the clinical symptoms, and collecting the nasal swabs, oral swabs and blood.

Safety Test

Nine of 30-40 kg FMDV serum antibody-negative healthy feeder pigs were randomly divided into 3 groups with 3 pigs in each group. The pigs in the first group were injected at posterior auricular muscle with rC351G attenuated strain at a dose of $10^6$ $TCID_{50}$/pig. Five days after the inoculation, slaughtering the first group of pigs, mixing and homogenizing the tonsil tissue, plasma, and oral and nasal secretion, and injecting 2 mL of the mixture into the second group of pigs. Similarly, slaughtering the second group of pigs after inoculated for 5 days, mixing and homogenizing the same tissues and samples, and injecting 2 mL of the mixture into the third group of pigs. Measuring the body temperature of each group of pigs, observing the clinical symptoms, and collecting the nasal swabs, oral swabs and blood daily after inoculation. And the third group of pigs had blood sampling performed 3 d, 7 d, 14 d, and 21 d after inoculation.

Vaccination and Challenge Test

In order to evaluate the immune-protective effect of the attenuated strain rC351G, 3 pigs were inoculated with this mutant, 2 pigs inoculated with PBS were used as the challenge controls. At 21 days post-vaccination, the O-type FMDV strain O/Mya-98/CHA/2010 which is currently prevalent in China was used to challenge the pigs to evaluate the immune-protective effect, the specific method is as follows:

Five of 20-30 kg FMDV serum antibody-negative healthy feeder pigs, 3 pigs were injected intramuscularly at cervical part with rC351G attenuated strain at a dose of $10^6$ $TCID_{50}$/pig, 2 pigs were injected intramuscularly at cervical part with 1 mL PBS as the controls. The immunized group and the control group were challenged at 21 days post-vaccination, each pig was injected intramuscularly at cervical part with O/Mya-98/CHA/2010 virus at a dose of 1000 $ID_{50}$/pig. Within 7 days after challenge, measuring the body temperature of each pig, observing the clinical symptoms, and collecting the nasal swabs, oral swabs and blood every day.

1.121 Clinical Symptoms Observation

Carefully observing and recording the clinical incidence of pigs daily, and performing the clinical scores according to the method described by Pacheco and Mason et al. (Pacheco and Mason et al., J. Vet. Sci., 2010): Clinical scores were based on the number of the sites containing vesicular lesions (three scores for each hoof, nose, tongue or lips), with a maximum score of 20 points.

1.122 Detection of the Viremia and Viral Shedding

The total RNA of the fresh nasal, oral swabs and blood samples were extracted using TRIZOL method, and were reversely transcribed using Oligo $(dT_{15})$ primer to obtain the cDNA used as a template, and the fluorescent quantitative PCR detection was performed using the FMDV specific primers (3DF: 5' GGA TGC CGT CTG GTT GTT 3' (SEQ ID NO: 38); 3DR: 5' CGT AGG AGA TCA TGG TGT AAG AGT 3' (SEQ ID NO: 39)). The specific operation of the fluorescent quantitative PCR is performed according to the kit instructions of Platinum® SYBR® Green qPCR Super Mix-UDG with ROX (Invitrogen), and the content of genomic RNA of virus in the samples are calculated by a standard curve. The background value of FMDV RNA amplified by using the blood, oral and nasal swab samples of preclinical healthy pigs through PCR amplification was 2.6 ($\bar{x}$+SD=2.26+0.34) log 10, and if the viral RNA copy number/ml (viral RNA CN/ml) is higher than this value, it is judged as FMDV-RNA-positive.

1.123 FMDV Specific Antibody Detection

The whole blood of pig was collected every day, the serum fraction separated was used to detect FMDV antibodies, and operate according to the instructions of the 0-type FMDV antibody liquid-phase blocking ELISA kit produced by the Foot and Mouth Disease Reference Laboratory of Lanzhou Veterinary Research Institution. Setting two wells for each serum dilution plate at a ratio of 1:2 and 1:4 as the negative controls, four wells of 1:16, 1:32, 1:64, 1:128 as the positive controls, and the virus antigen was set 4 wells as the controls. The serum to be tested is successively diluted from 1:8 to 1:1024 by double dilution method.

Each step of the reaction was carried out according to the instructions. After the reaction was terminated, the $OD_{450\ nm}$ values were measured by a microplate reader.

1.124 Antibody Detection of FMDV Non-Structural Protein 3ABC

The whole blood of pig was collected every day, the serum fraction separated was used to detect the antibodies of FMDV non-structural protein 3ABC according to the instructions of the 3ABC-I-ELISA of the Foot-and-Mouth Disease Reference Laboratory of Lanzhou Veterinary Research Institution. Diluting serum in 96-well ELISA plates, and setting two wells for the negative and positive controls, respectively. Diluting 6 µL of serum into 120 µL of serum diluent with a dilution of 1:21, one repetition is set per diluted serum, and diluting 46 serum per plate, adding dropwise the diluted serum to the ELISA coated plate. After reacting for a certain period of time, various enzyme labeling reagents and substrates were sequentially added, and finally the absorbance values ($OD450_{nm}$ value) at a wavelength of 450 nm were measured by a microplate reader. Antibody titer=($OD_{450\ nm}$ sample $-OD_{450\ nm}$ negative)/($OD_{450\ nm}$ positive $-OD_{450\ nm}$ negative), if this value >0.2, it is judged as positive.

1.125 Micro-Neutralization Assay

First, the $TCID_{50}$ of FMDV O/YS/CHA/05 virus was determined using BHK-21 cells, and then the micro-neutralization test was carried out by using the method of fixing virus diluted serum. Inactivating the serum at 56° C. for 30 min, and performing doubling dilution using PBS. Mixing 100 $TCID_{50}$ of virus with different dilutions of serum in equal volume, and incubating for 1 h at 37° C.; the above serum-virus mixtures (100 µL/well) were inoculated into BHK-21 cells respectively, 8-well repeats per titer, culturing at 37° C. in a 5% $CO_2$ incubator, observing the CPE daily, and making the final determination after 72 hours. In addition, setting the virus, positive serum and normal cell controls. The virus neutralization titer was calculated according to the CPE by using the Reed-Muench method (Reed and Muench., 1938). The virus neutralization titer was the serum dilution concentration that can protect 50% of BHK-21 cells from CPE.

1.126 Indirect ELISA

The FMDV serum antibody-negative pigs were screened using the indirect ELISA methods to detect three serotypes (Type-O, Type-A, and Type-Asia1) of FMDV antibody. The specific steps are as follows: using the inactivated and purified FMDV whole virus as an antigen, coating the 96-well ELISA plate, and adding 5% skim milk for sealing overnight at 4° C.; washing 3 times with PBST, and then adding the serum to be tested, 100 µL per well, incubating at 37° C. for 1 h, washing 3 times with PBST, and adding 100 µL of HRP-labeled goat anti-porcine IgG (1:5000) per well as a secondary antibody (Sigma), incubating at 37° C. for 1 h; washing 3 times with PBST, adding 50 µL/well of TMB substrate color-developing solution, performing light-proof reaction at 37° C. for 15 min; adding 50 µL/well of 2M $H_2SO_4$ to stop the reaction, and finally determining the $OD_{450\ nm}$ value by microplate reader.

2. Results 2.1 IRES Chimeric Virus FMDV(R4) is an Attenuated Mutant

Figures 1, 2:
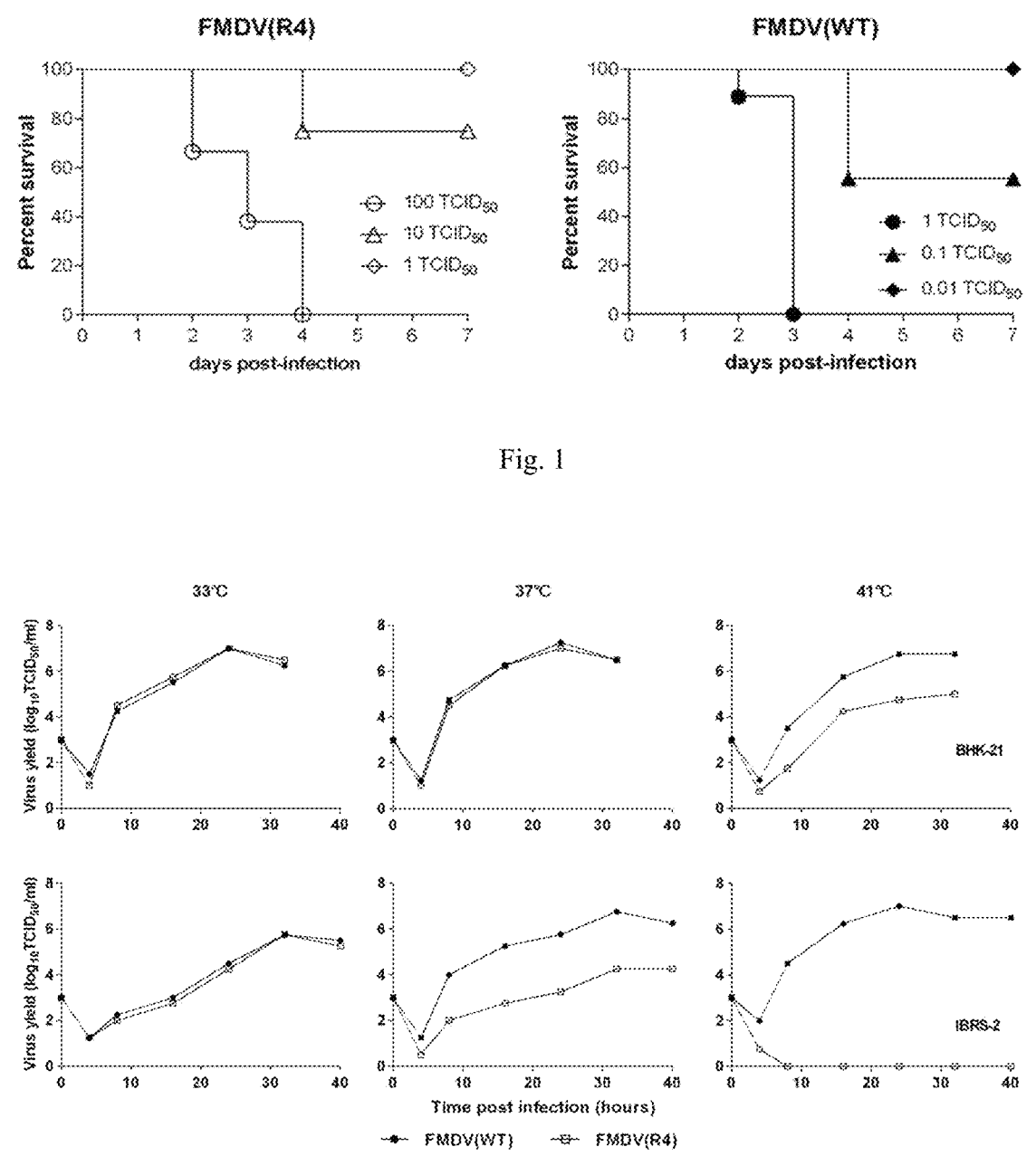

The present invention uses the Type-O FMDV reverse genetic operating system to replace the domain 4 of FMDV IRES with the corresponding domain of BRBV IRES, and successfully constructs and rescues the IRES chimeric mutant FMDV(R4). The suckling mouse is a well-recognized animal model for evaluating the virulence of FMDV, thus 3-day-old suckling mice are used as models, and the virulence of the IRES chimeric virus FMDV(R4) and its wild-type virus FMDV(WT) have been determined and compared, the test results are shown in FIG. 1. For FMDV (WT), 1 $TCID_{50}$ of virus inoculation dose caused the death of all suckling mice, 0.1 $TCID_{50}$ of virus inoculation dose caused partial (50%) of suckling mice to die, while 0.01 $TCID_{50}$ of virus inoculation dose did not cause the death of suckling mice; for IRES chimeric virus FMDV(R4) strain, 100 $TCID_{50}$ of virus inoculation dose caused the death of all suckling mice, 10 $TCID_{50}$ of virus inoculation dose caused partial (80%) of suckling mice to die, while 1 $TCID_{50}$ of virus inoculation dose did not cause the death of suckling mice. The above results showed that the virulence of IRES domain 4 chimeric virus FMDV(R4) to suckling mice significantly decreased, and the virulence thereof decreased by about 100 times compared with that of the parental virus FMDV(WT), demonstrating that domain 4 of IRES is the determinant factor of the virulence of FMDV.

2.2 FMDV(R4) is a Temperature-Sensitive Mutant

To investigate the mechanism of FMDV virulence attenuation caused by replacement of IRES domain 4, we firstly analyzed the secondary structure stability of the domain 4-chimeric IRES compared to wild-type FMDV IRES using M-fold software (version 3.2). As calculated by M-fold, the ΔG value of FMDV(R4) IRES was higher (−185.40 kcal/mol) than that of FMDV(WT) (−196.60 kcal/mol), indicating that the structure of FMDV(R4) IRES was less stable. In addition, BRBV replication is normally confined to the cooler upper respiratory tract epithelium, and is naturally temperature-sensitive when grew at elevated temperatures. Getting together we have reason to assume that the FMDV (R4), in which the IRES domain 4 was replaced by that of BRBV, is a temperature-sensitive and thus attenuated mutant.

In order to investigate whether the replication of FMDV (R4) is temperature-sensitive, one-step growth curves of FMDV(R4) at different temperatures in hamster-derived BHK-21 and porcine-derived IBRS-2 cells were plotted. The results are shown in FIG. 2. In BHK-21 cells, the replication ability of FMDV(R4) was slightly higher than that of FMDV(WT) at 33° C.; and the replication ability of FMDV(R4) was slightly lower than that of FMDV(WT) at 37° C.; whereas, the replication ability of chimeric virus FMDV(R4) significantly decreased, which decreased by about 100 times compared with that of the parental virus FMDV(WT) at 41° C. In IBRS-2 cells, the chimeric virus FMDV(R4) has similar proliferation properties to the parental FMDV(WT) at 33° C.; and the replication ability of chimeric virus FMDV(R4) significantly decreased, which decreased by about 100 times compared with that of parental virus FMDV(WT) at 37° C.; at 41° C., the replication ability of chimeric virus FMDV(R4) was almost lost, but its parental virus FMDV(WT) can still achieve a high replication titer ($10^{6.25}$ $TCID_{50}$/ml). The above results confirmed that the IRES chimeric attenuated strain FMDV(R4) is a temperature-sensitive mutant, and this temperature sensitivity is very significant in the porcine-derived IBRS-2 cells.

2.3 the K Region of IRES Domain 4 Determines the Temperature-Sensitive Attenuated Phenotype of FMDV(R4)

Figures 3, 4:
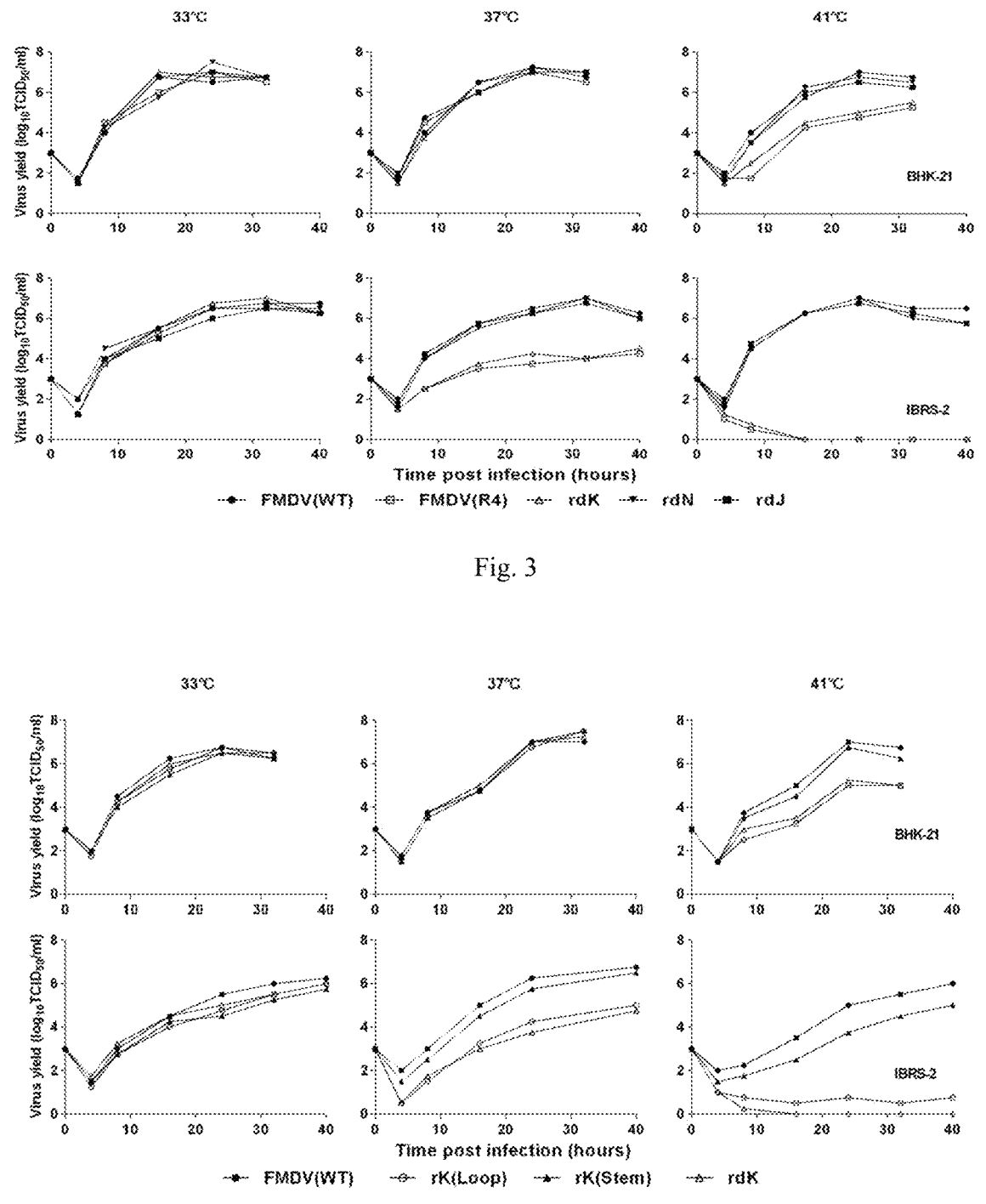

In order to further analyze the molecular determinants of the temperature-sensitive attenuated phenotype of the IRES chimeric virus FMDV(R4), the present invention uses the type-O FMDV reverse genetic system to replace the J, K, and N subdomains in domain 4 of FMDV IRES with the corresponding subdomains of BRBV IRES. Three IRES J, K and N subdomains chimeric FMDV mutant were successfully constructed and rescued, respectively named rdJ, rdK and rdN. The replication dynamics of the three chimeric viruses at different temperatures were determined and analyzed, and the one-step growth curves were plotted. The test results are shown in FIG. 3. Whether in BHK-21 cells or IBRS-2 cells, or at different temperatures of 33° C., 37° C. and 41° C., the chimeric viruses rdJ, rdN and the parental virus FMDV(WT) had similar proliferation properties. However, in BHK-21 cells, the chimeric virus rdK had the similar replication ability to the parental virus FMDV(WT) at 33° C. and 37° C., but the replication ability significantly decreased at 41° C., which decreased by about 100 times compared with that of the parental virus FMDV(WT); in IBRS-2 cells, the replication ability of chimeric virus rdK significantly decreased even at 37° C., which decreased by about 100 times compared with that of the parental virus, and the replication ability of rdK was almost lost at 41° C. The replication properties of the chimeric virus rdK (rather than rdJ and rdN) were consistent with the replication properties of the chimeric virus FMDV(R4), indicating that the K region of IRES domain 4 determined the temperature-sensitive properties of the chimeric virus FMDV(R4). At the same time, the virulence test results in the suckling mice showed that the virulence of rdK decreased by about $10^6$ times compared with the virulence of FMDV(WT) (FIG. 7). To sum up, the above results indicated that the K region of IRES domain 4 determines the temperature-sensitive attenuated phenotype of the IRES chimeric virus FMDV(R4).

2.4 the Loop Structure of the K Region of the IRES Domain 4 Determines the Temperature-Sensitive Attenuated Phenotype of FMDV(R4)

Figure 6:
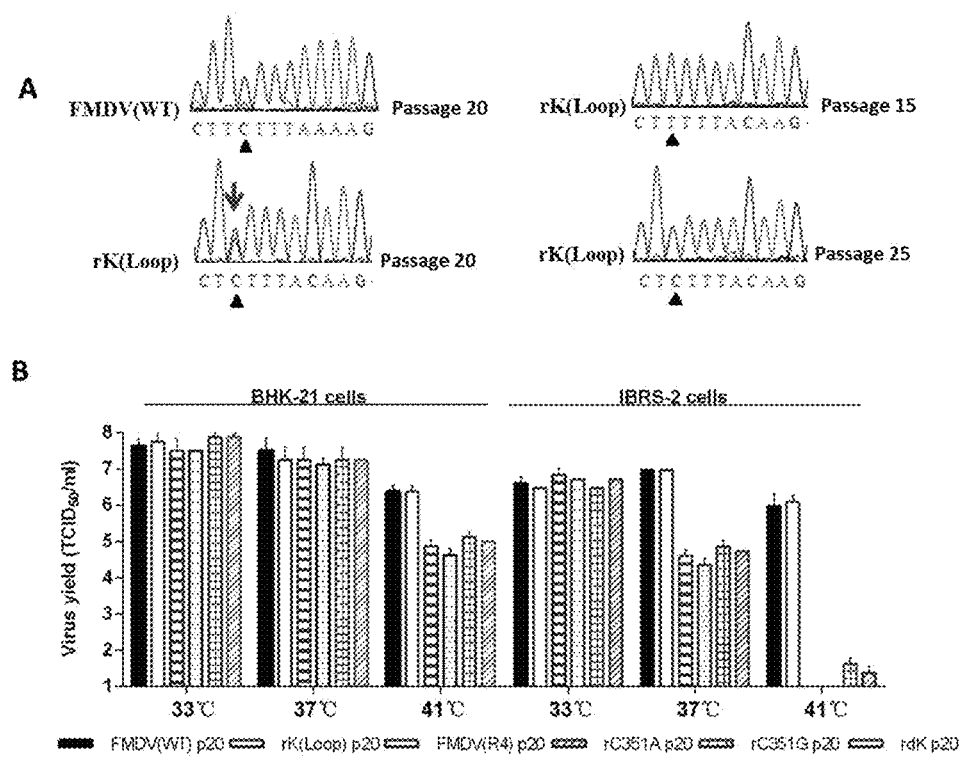

The K regions of the IRES domain 4 of FMDV and BRBV are respectively composed of a stem-loop structure. In order to determine the region in the stem-loop structure of the K region associated with the temperature-sensitive attenuated phenotype of FMDV, the present invention uses the reverse genetic system to replace the stem or loop of the K region of the FMDV IRES with the counterpart region of the BRBV IRES. The two chimeric viruses rescued were named rK(Stem) and rK(Loop), respectively. The replication dynamics of the two chimeric viruses in different cells were determined at different temperatures, and the one-step growth curves are shown in FIG. 4. Whether in BHK-21 cells or IBRS-2 cells, or at different temperatures of 33° C., 37° C. and 41° C., the chimeric virus rK(Stem) has similar proliferation properties to the parental virus FMDV(WT); however, the replication abilities of chimeric virus rK(Loop) in the two kinds of cells gradually decreased with the increase of temperature, and its replication properties were extremely similar to those of rdK. The above results indicated that the loop structure of the K region of IRES domain 4 determined the temperature sensitivity of the chimeric virus FMDV(R4). The virulence of rK(Loop) was determined, and it was found that the virus was unstable in suckling mice, a T351C reverse mutation occurred at the 351-site of IRES, which is consistent with the reverse mutation occurred at the 351-site of IRES after the virus was subjected to multiple passages in vitro cells (FIG. 6A); this reverse mutation results in the loop structure of the K region of the rK(Loop) being close to the loop structure of the K region of the parental virulent strain, and thus the virulence of the mutant rK(Loop) to the suckling mouse restored to the level of the parental virus (FIG. 7).

2.5 Nucleotide C at 351-Site on the Loop of K Region of IRES Domain 4 Determines the Temperature-Sensitive Attenuated Phenotype of FMDV Alignment analysis revealed that the loop sequence ($^{351}$CUUUAA$^{356}$) in IRES subdomain K of FMDV is different to that of BRBV (UUUAC), including one more nucleotide at 351 position in the IRES of FMDV, and one nucleotide difference at 356 position (A for FMDV or C for BRBV) between the IRESes of two viruses. To test which nucleotide in the loop of subdomain K determined the temperature-sensitive attenuated phenotypes of FMDV, single point mutation was performed in the infectious cDNA clones of FMDV. Firstly, we generated a mutant rA356C with a single-nucleotide substitution at 356 position of IRES. The replication dynamics (FIG. 5) of the mutant virus at different temperatures showed that the replication abilities of rA356C in the two kinds of cells, BHK-21 and IBRS-2, were similar to those of the parental virus FMDV(WT) at 33° C., 37° C. and 41° C., which indicated that the nucleotide A356 of FMDV IRES was irrelevant to the temperature-sensitive phenotype of FMDV.

In order to determine whether the nucleotide C351 of IRES determines the temperature-sensitive phenotype of FMDV, the present invention makes the following four mutations for the nucleotide C at the 351 position:

(1) a deletion of nucleotide C351; (2) nucleotide C351 mutated to nucleotide A; (3) nucleotide C351 mutated to nucleotide G; (4) nucleotide C351 mutated to nucleotide U.

Figure 5:
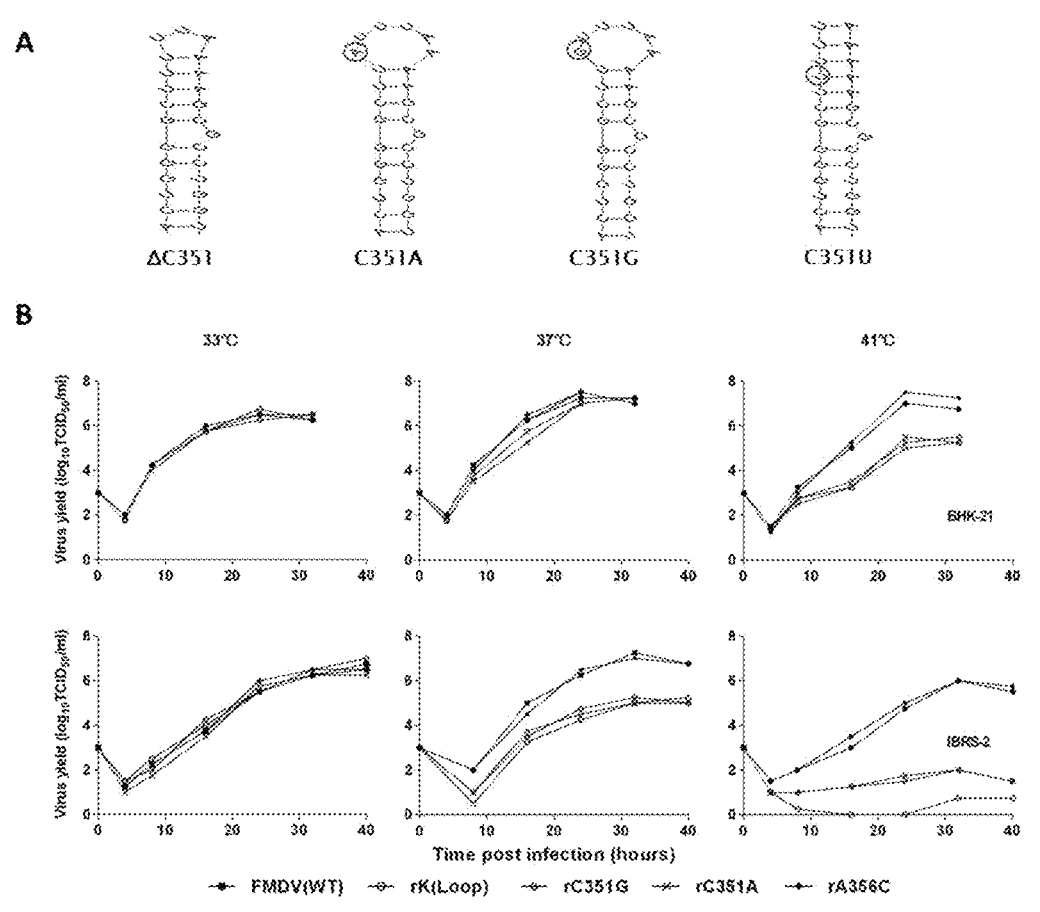

The final test results showed that the mutation schemes (1) and (4) failed to rescue the virus due to the destruction of the loop structure of the IRES (FIG. 5A), while the mutation schemes (2) and (3) can rescue the virus due to the of invariance of the IRES loop structure (FIG. 5A), and the rescued mutants are named rC351A and rC351G, respectively. The replication dynamics of these two IRES point mutant viruses at different temperatures were measured, and the results are shown in FIG. 5. In BHK-21 cells, the rC351G, rC351A and the parental virus FMDV(WT) had similar proliferation properties at 33° C. and 37° C., when the temperature rose to 41° C., the replication abilities of rC351G and rC351A decreased by 100 times compared with that of parental virus. In porcine-derived IBRS-2 cells, the replication abilities of rC351G and rC351A decreased gradually with the increase of temperature compared with that of the parental virus, and the replication levels of rC351G and rC351A decreased significantly by 10,000 times compared with that of the parental virus at 41° C. The above results showed that the replication properties of the two IRES 351-site nucleotide C point mutant viruses were similar to that of the IRES chimeric virus rK(Loop), indicating that this site is the molecular determinant of the temperature-sensitive phenotype of IRES chimeric FMDV. At the same time, it was also found that the virulence of FMDV temperature-sensitive mutants mutated at IRESC351-site significantly decreased to suckling mice. Compared with wild-type virus, the virulence of rC351G decreased by about 10,000 times and the virulence of rC351A decreased by about 1,000 times. To sum up, the above results finally indicate that the nucleotide C at 351 position on the loop of the K region of IRES domain 4 determines the temperature-sensitive attenuated phenotype of FMDV.

2.6 Genetic Stability of Temperature-Sensitive Attenuated Strains for Continuous Passage In Vitro In order to determine the genetic stability of FMDV temperature-sensitive attenuated strains, in the present invention, the IRES chimeric or site-directed mutagenesis viruses FMDV(R4), rdK, rK(Loop), rC351G, rC351A and the parental virus FMDV(WT) were continuously passaged for 20 times in BHK-21 cells, and the IRES sequences of 20$^{th}$ passage viruses were determined. For 20 passages in BHK-21 cells, the IRES sequences of FMDV(R4), rdK, rC351G and rC351A did not have any mutation; moreover, the mutant viruses still retained their original temperature-sensitive properties in cells (FIG. 6B) and the attenuated phenotypes in suckling mice (FIG. 7). However, although rK(Loop) did not have any occurrences of any mutations until the 15$^{th}$ passage, and in the 20th passage, some viruses had T351C mutations at the IRES 351 position. The viruses of rK(Loop) were continue passaging for 5 times, and the T351C mutant viruses became the dominant clones (FIG. 6A); meanwhile, the 25$^{th}$ passage viruses of rK(Loop) lost the temperature-sensitive properties (FIG. 6B), and their virulence to suckling mice reversed to a level similar to that of wild-type virus (FIG. 7). The above results showed that the IRES chimeric or site-directed mutagenesis mutants of FMDV, FMDV(R4), rdK, rC351G and rC351A, had high genetic stability; whereas the IRES K-region loop chimeric FMDV, rK(Loop), is unstable. When it was passed to the 20$^{th}$ passage, the reverse mutation occurred in some of the virus, and when it was passed to the 25$^{th}$ passage, the reverse mutation occurred in the whole virus group.

Figure 8:
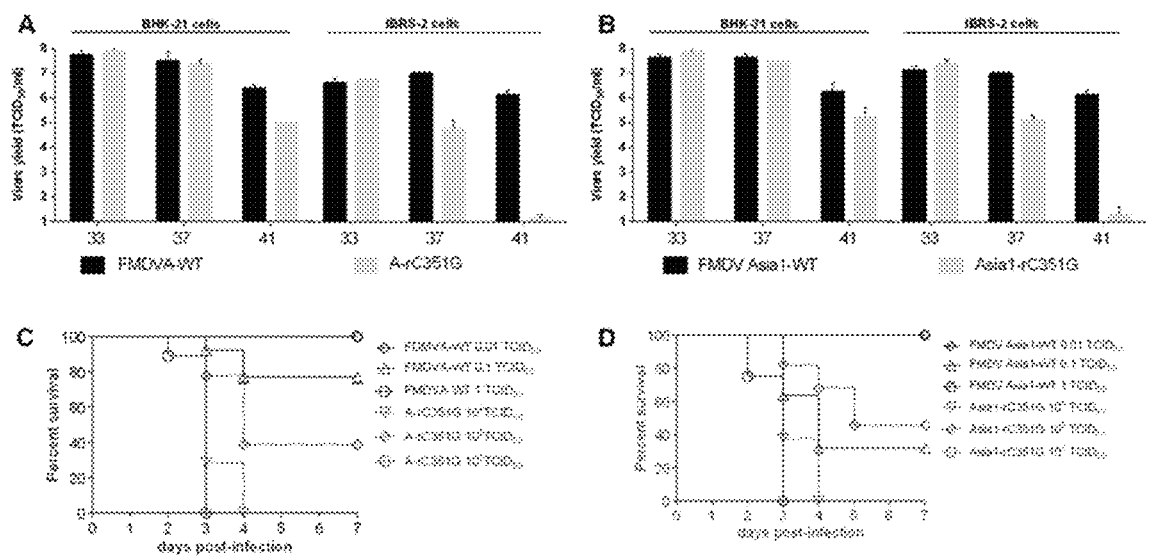
FIG. 8 is a graph showing the temperature sensitivities (A and B) in cells and virulence (C and D) in suckling mice of the type-A and type-Asia1 FMDV IRES C351G mutants thereof.

2.7 IRES C351 is the Determining Site for Temperature-Sensitive Attenuated Phenotype Shared by FMDV Strains Although both rC351G and rC351A have high genetic stability, the attenuating effect of rC351G is more obvious than that of rC351A. Therefore, rC351G and C351G mutant IRES are selected as the research objects in the subsequent studies. The above research results were all produced using the type-O FMDV strains. In order to verify that the C351G mutation of IRES also determines the temperature-sensitive attenuated phenotype of other serotypes of FMDV strains, the present invention further uses the full-length cDNA infectious clone of the type-A and type-Asia1 FMDV to construct and rescue viral mutants with the nucleotide substitution of C351G in the IRES, which are named A-rC351G and Asia1-rC351G, respectively. The temperature sensitivities of the above IRES mutants have been determined, and the results are shown in FIGS. 8A and 8B: the replication abilities of both A-rC351G and Asia1-rC351G in BHK-21 and IBRS-2 cells decreased with the increase of temperature, which indicated that the C351G mutation in the IRES also enabled other serotypes of FMDV strains to obtain the temperature-sensitive phenotype. In addition, the virulence test results of A-rC351G and Asia1-rC351G to suckling mice showed that the C351G mutation in the IRES could also reduce the virulence of the type-A and type-Asia1 FMDV to suckling mice by at least 10,000 times (FIGS. 8C and 8D), indicating that the temperature-sensitive attenuated phenotypes of the three serotypes of FMDV strains prevalent in China, type-O, type-A and type-Asia1, were determined by IRES C351. Since the C351 site of IRES and the functional stem-loop structure surrounding the site are conserved in all seven serotypes of FMDV strains, it is inferred that the IRES C351 is a molecular determinant of the temperature-sensitive attenuated phenotype in all serotypes of FMDV strains.

Figure 9:
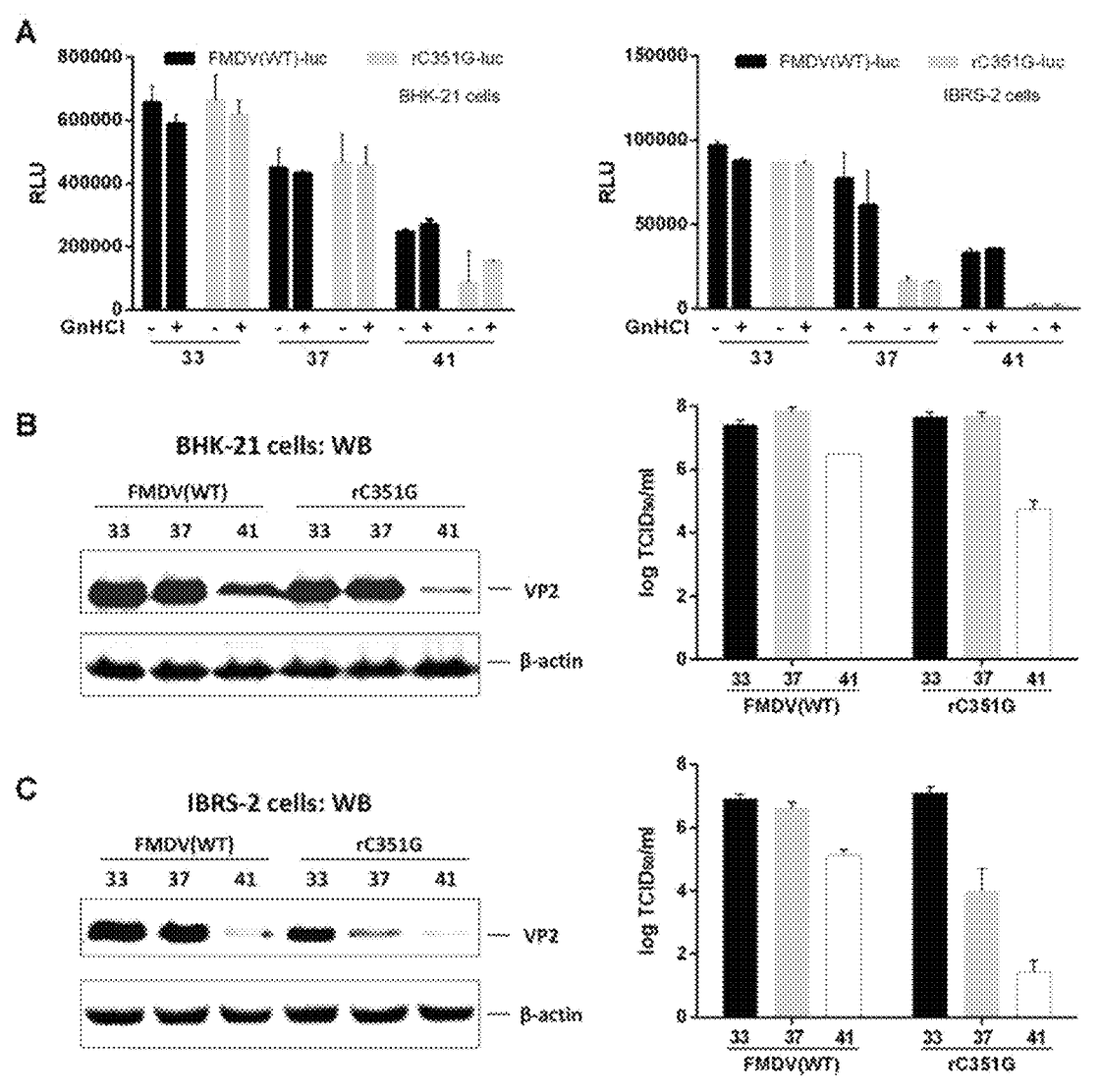

2.8 the Ability of the IRES C351G Mutant-Mediated Translation Initiation is Regulated by Temperature To explore the molecular mechanism causing the temperature-sensitive attenuated phenotypes of rC351G, we investigated a critical early step in viral replication, the initiation of IRES-directed translation of viral protein in a cap-independent manner. In order to achieve this, we constructed two luciferase replicons rC351G-luc and FMDV(WT)-luc, which contain the respective IRES elements in the same context as in their parent viruses, rC351G and FMDV(WT). The capacity of these luciferase replicons for IRES-mediated translation was assessed by transfecting BHK-21 and IBRS-2 cells with in vitro-transcribed replicon RNA at 33° C., 37° C. and 41° C., respectively. To differentiate the luciferase signal from translation of input viral RNA from the translation of newly replicated RNA, one portion of the transfected cells received 2 mM GnHCl, a potent inhibitor of FMDV RNA replication that has no toxic effects on cellular processes or viral translation. The results are shown in FIG. 9A, in BHK-21 cells, although the translation efficiencies of the IRES with C351G mutation were similar to those of wild-type IRES at 33° C. and 37° C., the translation efficiency thereof decreased significantly at 41° C.; in IBRS-2 cells, the translation initiation efficiency mediated by IRES with a C351G mutation decreased with the increase of temperature, the decrease was most obvious at 41° C., and the translation ability of the C351G-mutated IRES at this temperature was almost lost. This change in the translation initiation efficiency of the C351G-mutated IRES is consistent with the growth dynamics of the viral mutant rC351G in the BHK-21 and IBRS-2 cells at different temperatures, both of which exhibit temperature-sensitive property, and this temperature-sensitive property is behaving more obvious in the porcine-derived IBRS-2 cells. The above results indicate that the translation initiation efficiency of rC351G IRES is significantly inhibited by increased temperature, thereby affecting the replication ability and virulence of virus in a temperature-sensitive manner.

In order to further confirm the temperature-sensitive effect of the translational initiation mediated by the C351G-mutated IRES, the expression dynamics of VP2 structural protein of the IRES mutant rC351G and its parental virus FMDV(WT) were analyzed. The results are shown in FIGS. 9B and 9C, the expression amount of VP2 protein of rC351G in the BHK-21 and IBRS-2 cells decreased with the increase of temperature, especially in the porcine-derived cells IBRS-2, the expression of VP2 protein of the virus was almost lost at 41° C. This temperature-sensitive effect of the translation level of VP2 protein mediated by the C351G mutation is consistent with the changes of the replication titer of infectious virions of the rC351G in the porcine-derived IBRS-2 cells at different temperatures, indicating that the translation initiation ability of the IRES C351G mutant is regulated by temperature.

2.9 Virulence Test of Mutant rC351G to the Suckling Mice and Pigs

The test results of the virulence to suckling mice showed that the virulence of rC351G was reduced by about 10,000 times compared with the virulence of FMDV(WT) (FIG. 7).

Figure 10:
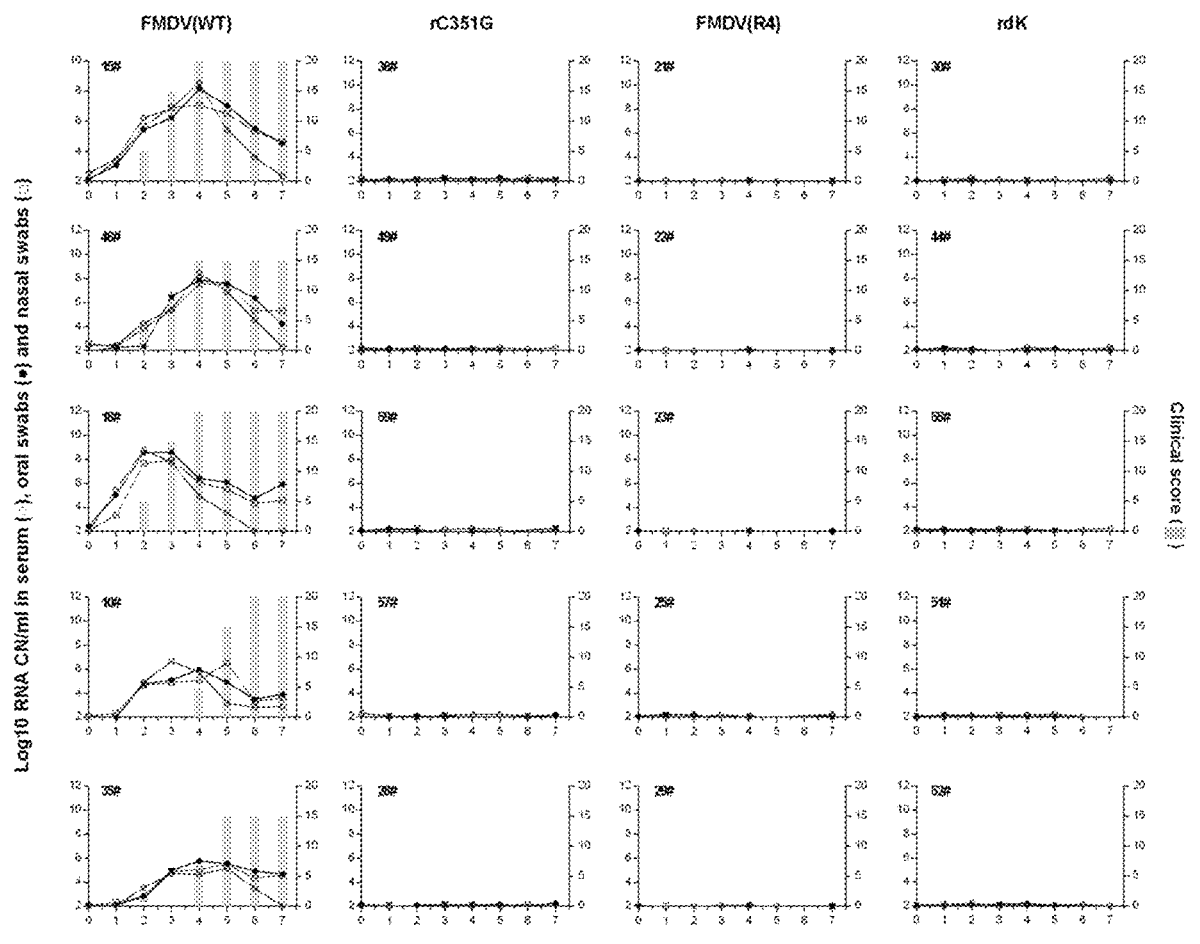

The test results of the virulence of rC351G strain returning to the pigs are shown in FIG. 10. Three pigs (15 #, 46 #, 18 #) were inoculated with 10$^5$ TCID$_{50}$ dose of wild-type virus FMDV(WT), and their body temperatures all reached 41° C. after inoculation for 48 hours, and the typical symptoms of FMD appeared, specifically manifested by decreased appetite, depression, lesions in both hoofs, mouth and nose; the inoculated pigs developed viremia only 1 day after vaccination. The amounts of the viral RNA in blood, oral and nasal swabs were significantly higher than the level of healthy pigs of 2.6 log$_{10}$ viral RNA CN/ml, and the viremia reached a peak of 8.7 log$_{10}$ RNA copies/ml at 4 dpi. The infection and incidence of the two cohabitation pigs (10 #, 35 #) were lagging behind those of the WT inoculated pigs, and their body temperatures reached 41° C. at 4 dpi (3 days after cohabitation), and lesions appeared in all four hoofs. Viral RNA in blood, oral and nasal swabs of cohabitation pigs were positive at 3 dpi, and reaching a peak of 7.1 $\log_{10}$ viral RNA CN/ml at 5 dpi. However, the attenuated mutant rC351G ($10^6$ TCID$_{50}$ per pig), equivalent to 10 times of the inoculated dose of the above wild-type virus, were inoculated into 3 pigs (36 #, 49 #, 59 #), and 2 pigs (57 #, 28 #) were used as cohabitation controls, and no clinical symptoms or increased body temperature occurred within 7 dpi; viral RNA in blood, oral and nasal swabs of the inoculated pigs and co-habiting pigs were all negative. Although rC351G inoculated pigs did not develop viremia, all the inoculated pigs produced the antibodies against FMDV non-structural protein 3ABC 21 days after inoculation, whereas, 3ABC antibodies of all the cohabiting pigs were test as negative for 21 days after inoculation, indicating that the attenuated strain rC351G showed partial replication at a low level in the vaccinated pigs, but did not develop viremia, did not shed virus or occur horizontal transmission. The above test results showed that the virulence of rC351G virus to suckling mice significantly decreased, and the virulence to the natural host pigs was lost.

2.10 Test Results of the Stability and Safety Evaluation of Attenuated Strain rC351G 1) In Vitro Cell Passage In order to test the genetic stability of the attenuated strain rC351G, continuous passage was performed in BHK-21 cells for 20 passages, and the whole genome sequence of the 20th passage virus was determined. The results showed that the rC351G strain had high genetic stability, and subjected to continuous passage for 20 passages in vitro, its IRES C351G did not undergo reversion mutation, and its attenuated phenotype did not change.

2) Co-Habiting Animals are not Infected

The results of cohabitation test are shown in FIG. 1. Healthy pigs (57 #, 28 #) do not show any clinical symptoms after cohabitating with rC351G vaccinated pigs (36 #, 49 #, 59 #). Detections of viral RNA in blood samples, oral and nasal swabs collected within 7 days were negative, and the antibody against FMDV non-structural protein 3ABC in the serum was also negative on the 21st day, indicating that no infection with FMDV rC351G occurred in cohabiting pigs. The above cohabitation test results showed that the pigs did not produce viremia and did not shed virus after inoculated with the attenuated mutant strain rC351G, the attenuated mutant strain rC351G has lost the virulence to susceptible animals, unable to horizontally transmit. Therefore, rC351G has excellent safety.

3) The Virulence does not Return to Virulent after Continuous Passage in Natural Host Animals To further evaluate the safety of the attenuated strain rC351G, the strain was performed continuous passage in piglets. The results showed that the attenuated strain rC351G was subjected to continuous passage for 3 passages in the body of pigs, inoculating 3 pigs per passage. All the pigs were normal in body temperature during the 5-day observation period and had no clinical symptoms. Serum antibodies of the third-passage vaccinated pigs, collected on the 3rd, 7th, 14th, and 21st day after inoculation, were tested. The results showed that anti-FMDV structural protein antibody was negative (LPBE value was less than 1:8), and the anti-FMDV non-structural protein 3ABC antibody was also negative (OD value <0.2), and viral RNA in blood, oral and nasal swabs were also negative on the 3rd, 7th, 14th, and 21st day after inoculation. The above test results showed that the attenuated strain rC351G did not return to virulent after being subjected to continuous passage in pigs, on the basis of the previous evidence that the co-habitation did not spread the virus, this further proved that the artificial inoculation and passage of the attenuated strain rC351G had good safety in vivo.

2.11 Test Results of the Immune Protective Effect of Attenuated Strain rC351G Immunized Pigs The test results of the immune protective effect of rC351G immunized pigs are shown in Tab. 3.

TABLE 3

Protection of the rC351G inoculated-pigs against challenged with FMDV O/Mya-98/CHA/2010 strains

| Inoculum | Challenging Dose (ID50) | Pig Number | Clinical Scoring (Onset Date) | Virus Isolation | Viral RNA Copy Number in Blood (Onset Date) | Viral RNA Copy Number in Nasal swabs (Onset Date) | Neutralizing Antibody Titer | |
|---|---|---|---|---|---|---|---|---|
| | | | | | | | 0dpc | 7dpc |
| rC351G | $10^3$ | 60 | 0 | negative | negative | negative | 128(180) | 512(720) |
| | | 66 | 0 | negative | negative | negative | 128(180) | 512(720) |
| | | 68 | 0 | negative | negative | negative | 64(90) | 256(360) |
| PBS | $10^3$ | 65 | 18(2) | positive | 8.7log10(3) | 8.5log10(3, 4) | <8(<8) | 128(180) |
| | | 73 | 16(3) | positive | 6.2log10(3) | 7.8log10(3, 4) | <8(<8) | 64(90) |

According to the test results, 2 days after the challenge, the body temperatures of two control pigs (65 #, 73 #) were increased to 41° C., the appetite decreased and the spirit was depressed, and 3 days after the challenge, the lesions appeared in the four hooves of the two pigs; 48 h after the challenge, the control pigs developed viremia, and the detections of FMDV RNA in blood, oral and nasal swabs were positive, the viremia reached a peak of 8.7 $\log_{10}$ viral RNA CN/ml 3 days after the challenge, at this time, the virus can be isolated from blood and from oral and nasal swabs. However, the 3 pigs (60 #, 66 #, 68 #) inoculated with the attenuated strain rC351G did not have any clinical symptoms or phenomenon of increasing body temperature within 7 days after the challenge, and the tests of the FMDV RNA, in the blood, oral and nasal swabs of the immunized pigs, were also negative, and the virus isolation was also negative; the results of FMDV antibody test after the challenge showed that the neutralizing antibody titer of FMDV 0 increased slightly from 1:128 to 1:512 and the titer of LPBE antibody increased from 1:180 to 1:720 at 7 dpc in the rC351G immunized group. In the PBS control group, the level of FMDV neutralizing antibody increased rapidly from less than 1:8 to 1:128, and the level of LPBE antibody also rapidly increased from 1:8 to 1:180. The results of the challenge test showed that the attenuated strain rC351G-immunized pigs could provide complete anti-infective protection against the challenge of currently popular type-O FMDV different genotype strains.

2.12 the Virulence of FMDV(R4) and rdK in Pigs

Three pigs were inoculated with the attenuated mutants FMDV(R4) or rdK ($10^6$ TCID$_{50}$ per pig), and after 24 hours, two native pigs were placed in each group for co-habitation. The results are shown in FIG. 10, none of the pigs showed any clinical symptoms or increasing body temperature throughout the experimental period; No viral RNA was detectable in the blood, oral and nasal swabs of the inoculated pigs and directly contacted pigs. 21 days after inoculation, the FMDV antibody test results showed that the FMDV neutralizing antibodies of all vaccinated pigs and cohabiting pigs were negative (<1:8). These results showed that the mutant FMDV(R4) and rdK had lost the infectivity to the natural host, and no viremia, no virus shedding, no horizontally transmitting, and no antibody developing. Therefore, as a virus-seed of inactivated vaccine, the attenuated mutants FMDV(R4) and rdK have better safety.

What is claimed is:

1. A construction method of a temperature-sensitive attenuated FMDV strain, comprising: constructing a FMDV full-length cDNA infectious cloning plasmid, performing a site-directed mutagenesis to an IRES region of the FMDV full-length cDNA infectious cloning plasmid, obtaining a FMDV genomic RNA by in vitro transcription, and transfecting the FMDV genomic RNA into cells and culturing the cells containing the FMDV genomic RNA at temperatures to rescue the temperature-sensitive attenuated FMDV strain; wherein a cytosine at 351-site on K region loop of IRES domain 4 of the FMDV genomic RNA obtained by the in vitro transcription is mutated to a guanine or an adenine during the site-directed mutagenesis, a base sequence of the K region loop after mutation is $^{351}$GUUUAA$^{356}$ or $^{351}$AUUUAA$^{356}$.

2. A temperature-sensitive attenuated FMDV strain obtained by the construction method according to claim 1, wherein a microbial deposit number of a full-length cDNA infectious cloning plasmid for rescuing the temperature-sensitive attenuated FMDV strain is: CGMCC NO.13148.

3. A mutant IRES contained in the temperature-sensitive attenuated FMDV strain according to claim 2, wherein the mutant IRES has the nucleotide sequence of SEQ ID No: 1.

4. A construction method of a temperature-sensitive attenuated FMDV strain, comprising: constructing a FMDV full-length cDNA infectious cloning plasmid, obtaining a FMDV genomic RNA by in vitro transcription, and transfecting the FMDV genomic RNA into cells to rescue the temperature-sensitive attenuated FMDV strain; wherein an IRES domain 4 of the FMDV genomic RNA obtained by the in vitro transcription is replaced with an IRES domain 4 of a bovine rhinovirus genomic RNA.

5. A temperature-sensitive attenuated FMDV strain obtained by the construction method according to claim 4, wherein a microbial deposit number of a full-length cDNA infectious cloning plasmid used for rescuing the temperature-sensitive attenuated FMDV strain is: CGMCC NO.13149.

6. A chimeric IRES sequence obtained by replacing an IRES domain 4 of a foot-and-mouth disease virus genomic RNA with an IRES domain 4 of a bovine rhinovirus genomic RNA, wherein the chimeric IRES sequence has the nucleotide sequence of SEQ ID No: 2.

7. A construction method of a temperature-sensitive attenuated FMDV strain, comprising: constructing a FMDV full-length cDNA infectious cloning plasmid, obtaining a FMDV genomic RNA by in vitro transcription, and transfecting the FMDV genomic RNA into cells to rescue the temperature-sensitive attenuated FMDV strain; wherein a K region of an IRES domain 4 of the FMDV genomic RNA obtained by the in vitro transcription is replaced with a K region of IRES domain 4 of a bovine rhinovirus genomic RNA.

8. A temperature-sensitive attenuated FMDV strain obtained by the construction method according to claim 7, wherein a microbial deposit number of a full-length cDNA infectious cloning plasmid used for rescuing the temperature-sensitive attenuated FMDV strain is: CGMCC NO.13150.

9. A chimeric IRES sequence obtained by replacing a subdomain K of FMDV IRES domain 4 with a subdomain K of IRES domain 4 of a bovine rhinovirus, wherein the chimeric IRES sequence has the nucleotide sequence of SEQ ID No: 3.

* * * * *

SEQUENCE LISTING

```
<160> NUMBER OF SEQ ID NOS: 40

<210> SEQ ID NO 1
<211> LENGTH: 438
<212> TYPE: DNA
<213> ORGANISM: Artificial Sequence
<220> FEATURE:
<223> OTHER INFORMATION: a synthesized nucleotide sequence of the IRES
      mutant
<220> FEATURE:
<221> NAME/KEY: misc_feature
<222> LOCATION: (351)..(351)
<223> OTHER INFORMATION: n is g or a

<400> SEQUENCE: 1
gtgcaacttg gaactccgcc tggtctttcc aggtctagag gggtgacatt ttgtactgtg      60
cttgactcca cgctcggtcc actggcgagt gctagtaaca gcactgttgc ttcgtagcgg     120
agcatggtgg ccgcgggaac tcctccttgg taacagggac ccgcggggcc gaaagccacg     180
tcctcacgga cccaccatgt gtgcaacccc agcacggcaa ctttattgtg aaaaccactt     240
taaggtgaca ctgatactgg tactcaacca ctggtgacag gctaaggatg cccttcaggt     300
accccgaggt aacacgcgac actcgggatc tgagaagggg actggggctt ntttaaaagc     360
gcctggttta aaaagcttct acgcctgaat aggtgaccgg aggccggcac ctttccttcg     420
aacaactgtc tttaaatg                                                    438

<210> SEQ ID NO 2
<211> LENGTH: 425
<212> TYPE: DNA
<213> ORGANISM: Artificial Sequence
<220> FEATURE:
<223> OTHER INFORMATION: a synthesized nucleotide sequence of a chimeric
      IRES sequence
<220> FEATURE:
<221> NAME/KEY: gene
<222> LOCATION: (1)..(277)
<223> OTHER INFORMATION: Foot-and-Mouth Disease Virus gene
<220> FEATURE:
<221> NAME/KEY: gene
<222> LOCATION: (278)..(374)
<223> OTHER INFORMATION: Bovine rhinovirus gene
<220> FEATURE:
<221> NAME/KEY: gene
<222> LOCATION: (375)..(425)
<223> OTHER INFORMATION: Foot-and-mouth disease virus gene

<400> SEQUENCE: 2
gtgcaacttg gaactccgcc tggtctttcc aggtctagag gggtgacatt ttgtactgtg      60
cttgactcca cgctcggtcc actggcgagt gctagtaaca gcactgttgc ttcgtagcgg     120
agcatggtgg ccgcgggaac tcctccttgg taacagggac ccgcggggcc gaaagccacg     180
tcctcacgga cccaccatgt gtgcaacccc agcacggcaa ctttattgtg aaaaccactt     240
```

```
taaggtgaca ctgatactgg tactcaacca ctggtgacag cctaaggatg ccctccaggt      300
acccccgggt aacaagtgac acccgggatc tgaggagggg actactttac gtagtttaaa      360
aaacgtctaa gctgaatagg tgaccggagg ccggcacctt ccttcgaac aactgtcttt       420 aaatg                                                                 425
```

```
<210> SEQ ID NO 3
<211> LENGTH: 426
<212> TYPE: DNA
<213> ORGANISM: Artificial Sequence
<220> FEATURE:
<223> OTHER INFORMATION: a synthesized nucleotide sequence of a chimeric
      IRES sequence
<220> FEATURE:
<221> NAME/KEY: gene
<222> LOCATION: (1)..(339)
<223> OTHER INFORMATION: Foot-and-Mouth Disease Virus gene
<220> FEATURE:
<221> NAME/KEY: gene
<222> LOCATION: (340)..(356)
<223> OTHER INFORMATION: Bovine rhinovirus gene
<220> FEATURE:
<221> NAME/KEY: gene
<222> LOCATION: (357)..(426)
<223> OTHER INFORMATION: Foot-and-mouth disease virus gene

<400> SEQUENCE: 3
gtgcaacttg gaactccgcc tggtctttcc aggtctagag gggtgacatt ttgtactgtg       60
cttgactcca cgctcggtcc actggcgagt gctagtaaca gcactgttgc ttcgtagcgg      120
agcatggtgg ccgcgggaac tcctccttgg taacagggac ccgcggggcc gaaagccacg      180
tcctcacgga cccaccatgt gtgcaacccc agcacggcaa ctttattgtg aaaaccactt      240
taaggtgaca ctgatactgg tactcaacca ctggtgacag gctaaggatg cccttccaggt     300 acccccgaggt aacacgcgac actcgggatc tgagaagggg actactttac gtagtttaaa     360
aagcttctac gcctgaatag gtgaccggag gccggcacct ttccttcgaa caactgtctt     420
taaatg                                                               426
```

```
<210> SEQ ID NO 4
<211> LENGTH: 51
<212> TYPE: DNA
<213> ORGANISM: Artificial Sequence
<220> FEATURE:
<223> OTHER INFORMATION: the sequence is synthesized

<400> SEQUENCE: 4
cgcagatctt aatacgactc actataggtt gaaaggggc gttagggtct c               51
```

```
<210> SEQ ID NO 5
<211> LENGTH: 56
<212> TYPE: DNA
<213> ORGANISM: Artificial Sequence
<220> FEATURE:
<223> OTHER INFORMATION: the sequence is synthesized

<400> SEQUENCE: 5
ctcggggtac ctgaagggca tccttaggct gtcaccagtg gttgagtacc agtatc         56
```

```
<210> SEQ ID NO 6
<211> LENGTH: 49
<212> TYPE: DNA
<213> ORGANISM: Artificial Sequence
<220> FEATURE:
<223> OTHER INFORMATION: the sequence is synthesized
```

<400> SEQUENCE: 6
tggtgacagc ctaaggatgc ccttcaggta ccccgaggta acacgcgac          49

<210> SEQ ID NO 7
<211> LENGTH: 50
<212> TYPE: DNA
<213> ORGANISM: Artificial Sequence
<220> FEATURE:
<223> OTHER INFORMATION: the sequence is synthesized

<400> SEQUENCE: 7
ggcctccggt cacctattca gcttagacgt tttttaaacc aggcgctttt          50

<210> SEQ ID NO 8
<211> LENGTH: 40
<212> TYPE: DNA
<213> ORGANISM: Artificial Sequence
<220> FEATURE:
<223> OTHER INFORMATION: the sequence is synthesized

<400> SEQUENCE: 8
cggaggccgg caccttcct tcgaacaact gtctttaacc          40

<210> SEQ ID NO 9
<211> LENGTH: 33
<212> TYPE: DNA
<213> ORGANISM: Artificial Sequence
<220> FEATURE:
<223> OTHER INFORMATION: the sequence is synthesized

<400> SEQUENCE: 9
gaggatatcg ctagctttga aaaccagtcg ttg          33

<210> SEQ ID NO 10
<211> LENGTH: 51
<212> TYPE: DNA
<213> ORGANISM: Artificial Sequence
<220> FEATURE:
<223> OTHER INFORMATION: the sequence is synthesized

<400> SEQUENCE: 10
cgcagatctt aatacgactc actataggtt gaaaggggc gttagggtct c          51

<210> SEQ ID NO 11
<211> LENGTH: 46
<212> TYPE: DNA
<213> ORGANISM: Artificial Sequence
<220> FEATURE:
<223> OTHER INFORMATION: the sequence is synthesized

<400> SEQUENCE: 11
ttgttacccc ggggtacctg gagggcatcc ttagcctgtc accagt          46

<210> SEQ ID NO 12
<211> LENGTH: 51
<212> TYPE: DNA
<213> ORGANISM: Artificial Sequence
<220> FEATURE:
<223> OTHER INFORMATION: the sequence is synthesized

<400> SEQUENCE: 12
cgcagatctt aatacgactc actataggtt gaaaggggc gttagggtct c          51

<210> SEQ ID NO 13
<211> LENGTH: 40

```
<212> TYPE: DNA
<213> ORGANISM: Artificial Sequence
<220> FEATURE:
<223> OTHER INFORMATION: the sequence is synthesized

<400> SEQUENCE: 13
tcctcagatc ccgggtgtca cttgttaccc cggggtacct                          40

<210> SEQ ID NO 14
<211> LENGTH: 42
<212> TYPE: DNA
<213> ORGANISM: Artificial Sequence
<220> FEATURE:
<223> OTHER INFORMATION: the sequence is synthesized

<400> SEQUENCE: 14
cacccgggat ctgaggaggg gactgggget tctttaaaag cg                       42

<210> SEQ ID NO 15
<211> LENGTH: 33
<212> TYPE: DNA
<213> ORGANISM: Artificial Sequence
<220> FEATURE:
<223> OTHER INFORMATION: the sequence is synthesized

<400> SEQUENCE: 15
gaggatatcg ctagctttga aaaccagtcg ttg                                 33

<210> SEQ ID NO 16
<211> LENGTH: 51
<212> TYPE: DNA
<213> ORGANISM: Artificial Sequence
<220> FEATURE:
<223> OTHER INFORMATION: the sequence is synthesized

<400> SEQUENCE: 16
cgcagatctt aatacgactc actataggtt gaaaggggc gttagggtct c              51

<210> SEQ ID NO 17
<211> LENGTH: 46
<212> TYPE: DNA
<213> ORGANISM: Artificial Sequence
<220> FEATURE:
<223> OTHER INFORMATION: the sequence is synthesized

<400> SEQUENCE: 17 gcttttaaa ctacgtaaag tagtcccctt ctcagatccc gagtgt                    46

<210> SEQ ID NO 18
<211> LENGTH: 42
<212> TYPE: DNA
<213> ORGANISM: Artificial Sequence
<220> FEATURE:
<223> OTHER INFORMATION: the sequence is synthesized

<400> SEQUENCE: 18
ctttacgtag tttaaaaagc ttctacgcct gaataggtga cc                       42

<210> SEQ ID NO 19
<211> LENGTH: 33
<212> TYPE: DNA
<213> ORGANISM: Artificial Sequence
<220> FEATURE:
<223> OTHER INFORMATION: the sequence is synthesized

<400> SEQUENCE: 19
```
gaggatatcg ctagctttga aaaccagtcg ttg                                   33

<210> SEQ ID NO 20
<211> LENGTH: 57
<212> TYPE: DNA
<213> ORGANISM: Artificial Sequence
<220> FEATURE:
<223> OTHER INFORMATION: the sequence is synthesized

<400> SEQUENCE: 20
ctcgggatct gagaagggga ctggggcttt ttacaagcgc ctggtttaaa aagcttc        57

<210> SEQ ID NO 21
<211> LENGTH: 57
<212> TYPE: DNA
<213> ORGANISM: Artificial Sequence
<220> FEATURE:
<223> OTHER INFORMATION: the sequence is synthesized

<400> SEQUENCE: 21
gaagcttttt aaaccaggcg cttgtaaaaa gccccagtcc ccttctcaga tcccgag        57

<210> SEQ ID NO 22
<211> LENGTH: 57
<212> TYPE: DNA
<213> ORGANISM: Artificial Sequence
<220> FEATURE:
<223> OTHER INFORMATION: the sequence is synthesized

<400> SEQUENCE: 22
cactcgggat ctgagaaggg gactaccttt aagtagttta aaaagcttct acgcctg        57

<210> SEQ ID NO 23
<211> LENGTH: 57
<212> TYPE: DNA
<213> ORGANISM: Artificial Sequence
<220> FEATURE:
<223> OTHER INFORMATION: the sequence is synthesized

<400> SEQUENCE: 23
caggcgtaga agctttttaa actacttaaa ggtagtcccc ttctcagatc ccgagtg        57

<210> SEQ ID NO 24
<211> LENGTH: 58
<212> TYPE: DNA
<213> ORGANISM: Artificial Sequence
<220> FEATURE:
<223> OTHER INFORMATION: the sequence is synthesized

<400> SEQUENCE: 24
ctcgggatct gagaagggga ctggggcttg tttaaaagcg cctggtttaa aaagcttc       58

<210> SEQ ID NO 25
<211> LENGTH: 58
<212> TYPE: DNA
<213> ORGANISM: Artificial Sequence
<220> FEATURE:
<223> OTHER INFORMATION: the sequence is synthesized

<400> SEQUENCE: 25
gaagcttttt aaaccaggcg cttttaaaca gccccagtc cccttctcag atcccgag        58

<210> SEQ ID NO 26
<211> LENGTH: 58
<212> TYPE: DNA
<213> ORGANISM: Artificial Sequence
<220> FEATURE:
<223> OTHER INFORMATION: the sequence is synthesized

<400> SEQUENCE: 26
ctcgggatct gagaagggga ctggggctta tttaaaagcg cctggtttaa aaagcttc        58

<210> SEQ ID NO 27
<211> LENGTH: 58
<212> TYPE: DNA
<213> ORGANISM: Artificial Sequence
<220> FEATURE:
<223> OTHER INFORMATION: the sequence is synthesized

<400> SEQUENCE: 27
gaagcttttt aaaccaggcg cttttaaata agccccagtc cccttctcag atcccgag        58

<210> SEQ ID NO 28
<211> LENGTH: 58
<212> TYPE: DNA
<213> ORGANISM: Artificial Sequence
<220> FEATURE:
<223> OTHER INFORMATION: the sequence is synthesized

<400> SEQUENCE: 28
ctcgggatct gagaagggga ctggggcttt tttaaaagcg cctggtttaa aaagcttc        58

<210> SEQ ID NO 29
<211> LENGTH: 58
<212> TYPE: DNA
<213> ORGANISM: Artificial Sequence
<220> FEATURE:
<223> OTHER INFORMATION: the sequence is synthesized

<400> SEQUENCE: 29
gaagcttttt aaaccaggcg cttttaaaaa agccccagtc cccttctcag atcccgag        58

<210> SEQ ID NO 30
<211> LENGTH: 58
<212> TYPE: DNA
<213> ORGANISM: Artificial Sequence
<220> FEATURE:
<223> OTHER INFORMATION: the sequence is synthesized

<400> SEQUENCE: 30
cgggatctga aagggggact acctttacgt agtttaaaaa gcttctacgc ctgaatag        58

<210> SEQ ID NO 31
<211> LENGTH: 58
<212> TYPE: DNA
<213> ORGANISM: Artificial Sequence
<220> FEATURE:
<223> OTHER INFORMATION: the sequence is synthesized

<400> SEQUENCE: 31
caggcgtaga agcttttaa actacgtaaa ggtagtcccc ttctcagatc ccgagtgt        58

<210> SEQ ID NO 32
<211> LENGTH: 57
<212> TYPE: DNA
<213> ORGANISM: Artificial Sequence
<220> FEATURE:
<223> OTHER INFORMATION: the sequence is synthesized

<400> SEQUENCE: 32
ctcgggatct gagaagggga ctggggcttt ttaaaagcgc tggtttaaa aagcttc        57

<210> SEQ ID NO 33
<211> LENGTH: 57
<212> TYPE: DNA
<213> ORGANISM: Artificial Sequence
<220> FEATURE:
<223> OTHER INFORMATION: the sequence is synthesized

<400> SEQUENCE: 33
gaagcttttt aaaccaggcg cttttaaaaa gccccagtcc ccttctcaga tcccgag      57

<210> SEQ ID NO 34
<211> LENGTH: 58
<212> TYPE: DNA
<213> ORGANISM: Artificial Sequence
<220> FEATURE:
<223> OTHER INFORMATION: the sequence is synthesized

<400> SEQUENCE: 34
ctcgggatct gagaagggga ctggggcttg tataaaagcg cccagtttaa aaagcttc    58

<210> SEQ ID NO 35
<211> LENGTH: 58
<212> TYPE: DNA
<213> ORGANISM: Artificial Sequence
<220> FEATURE:
<223> OTHER INFORMATION: the sequence is synthesized

<400> SEQUENCE: 35
gaagcttttt aaactgggcg cttttataca agccccagtc cccttctcag atcccgag    58

<210> SEQ ID NO 36
<211> LENGTH: 58
<212> TYPE: DNA
<213> ORGANISM: Artificial Sequence
<220> FEATURE:
<223> OTHER INFORMATION: the sequence is synthesized

<400> SEQUENCE: 36
ctcgggatct gagaagggga ccgggacttg tttaaaagtg cccggtttaa aaagcttc    58

<210> SEQ ID NO 37
<211> LENGTH: 58
<212> TYPE: DNA
<213> ORGANISM: Artificial Sequence
<220> FEATURE:
<223> OTHER INFORMATION: the sequence is synthesized

<400> SEQUENCE: 37
gaagcttttt aaaccgggca cttttaaaca agtcccggtc cccttctcag atcccgag    58

<210> SEQ ID NO 38
<211> LENGTH: 18
<212> TYPE: DNA
<213> ORGANISM: Artificial Sequence
<220> FEATURE:
<223> OTHER INFORMATION: the sequence is synthesized

<400> SEQUENCE: 38
ggatgccgtc tggttgtt                                                 18

<210> SEQ ID NO 39
<211> LENGTH: 24
<212> TYPE: DNA
<213> ORGANISM: Artificial Sequence
<220> FEATURE:
<223> OTHER INFORMATION: the sequence is synthesized

```
<400> SEQUENCE: 39
cgtaggagat catggtgtaa gagt                                      24

<210> SEQ ID NO 40
<211> LENGTH: 26
<212> TYPE: DNA
<213> ORGANISM: Artificial Sequence
<220> FEATURE:
<223> OTHER INFORMATION: the sequence is synthesized

<400> SEQUENCE: 40
actagttaat acgactcact ataggg                                    26
```